United States Patent [19]

Rose et al.

[11] Patent Number: 5,439,793
[45] Date of Patent: Aug. 8, 1995

[54] METHOD FOR PRODUCING A POLYNUCLEOTIDE HAVING AN INTRAMOLECULARLY BASE-PAIRED STRUCTURE

[75] Inventors: Samuel Rose; Linda M. Western, both of Mountain View, Calif.

[73] Assignee: Syntex (U.S.A.) Inc., Palo Alto, Calif.

[21] Appl. No.: 555,968

[22] Filed: Jul. 19, 1990

[51] Int. Cl.$^6$ .......................... C12Q 1/68; C12P 19/34
[52] U.S. Cl. ........................................... 435/6; 935/77; 935/78; 435/91.2
[58] Field of Search .................. 435/6, 91, 91.1, 91.2; 436/501, 94; 935/77, 78; 536/27, 22.1

[56] References Cited

U.S. PATENT DOCUMENTS

| | | | |
|---|---|---|---|
| 4,683,195 | 7/1987 | Mullis et al. | 435/6 |
| 5,066,584 | 11/1991 | Gyllensten et al. | 435/91.2 |

FOREIGN PATENT DOCUMENTS

| | | | |
|---|---|---|---|
| 0224126 | 6/1987 | European Pat. Off. | 536/22.1 |
| 224995 | 6/1987 | European Pat. Off. | 435/6 |
| 379369 | 7/1990 | European Pat. Off. | 435/6 |
| 8909835 | 10/1989 | WIPO | 435/6 |
| WO90/11374 | 11/1990 | WIPO | 435/6 |

OTHER PUBLICATIONS

Georges et al., Nucl. & Nucl. 8(8):1427–1440 (1984).
Higgins et al., Meth. Enz. 68:50–71 (1979).
Hindley, in Work & Burdon, eds., Laboratory Techniques in Biochemistry & Molecular Biology, Elsevier Bio-Medical Press, Amsterdam, 1983. pp. 10–15.
Nelson et al., PNAS(USA) 86:6686–6690 (Sep. 1989).
Frohman et al., PNAS(USA) 85:8998–9002 (Dec. 1988).
Strobel et al., Molec. Cell. Biology 6(7):2674–2683 (Jul. 1986).
Watson et al., Molecular Biology of the Gene, 4th Edn., Benjamin/Cummings Publ. Co., Inc., Menlo Park, Calif., 1987. pp. 939–941.

*Primary Examiner*—Stephanie W. Zitomer
*Attorney, Agent, or Firm*—Theodore J. Leitereg

[57] ABSTRACT

A method is disclosed for forming a single stranded polynucleotide having two segments that are non-contiguous and hybridizable with each other. The method comprises the step of providing in combination (1) a first polynucleotide sequence having a hydroxyl at its 3'-end, (2) a second polynucleotide sequence having a hydroxyl or phosphate group at its 5'-end, and (3) a ligase, wherein at least ten consecutive bases of one of the sequences can hybridize to the other of the sequences to form a duplex. The duplex is comprised of a non-hybridized single stranded portion of one of the polynucleotide sequences containing one of the ends and at least five bases. The combination is provided under conditions for forming the duplex and ligating the ends within the duplex. The method finds particular application in the detection of polynucleotide analytes.

49 Claims, 5 Drawing Sheets

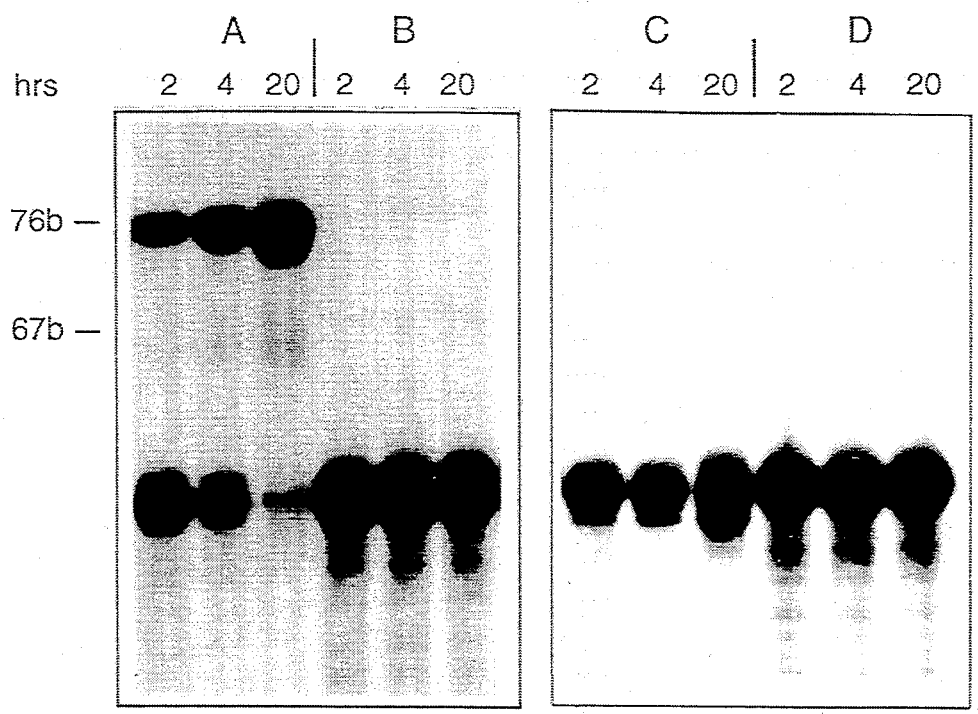
FIG._1
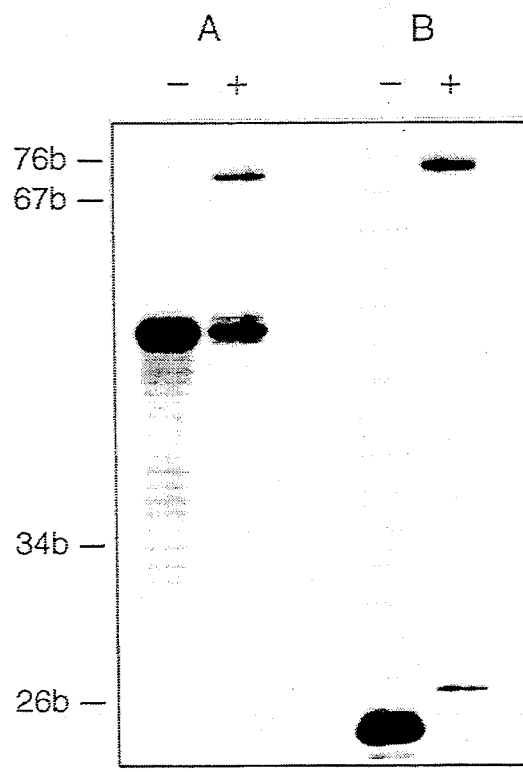
FIG._2

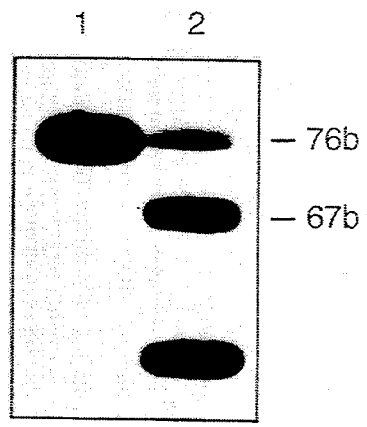
FIG._3
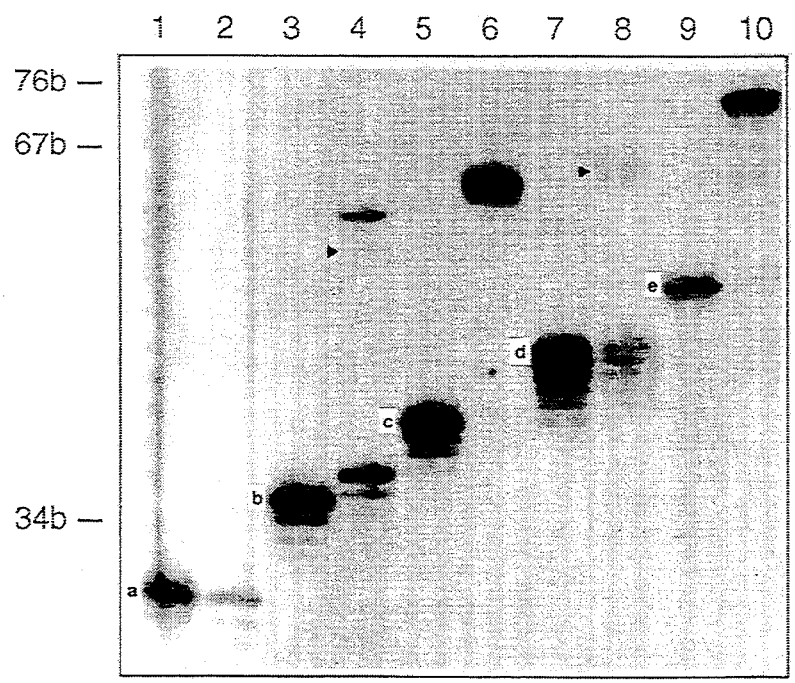
FIG._4

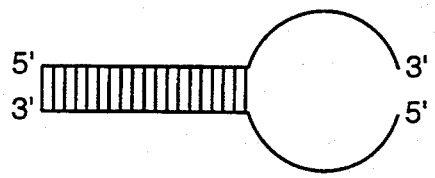
FIG._5
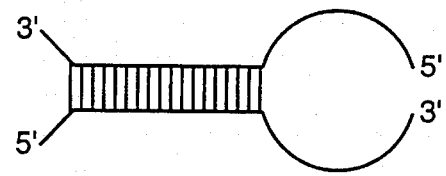
FIG._6
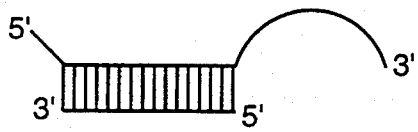
FIG._7
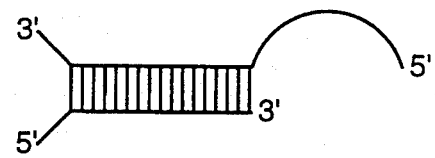
FIG._8
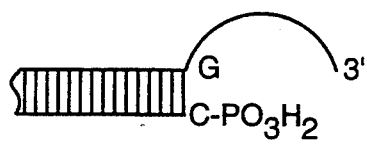
FIG._9
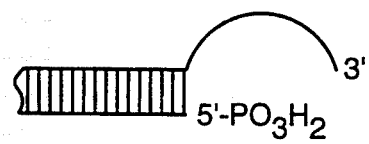
FIG._10
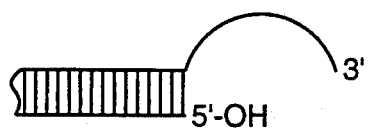
FIG._11
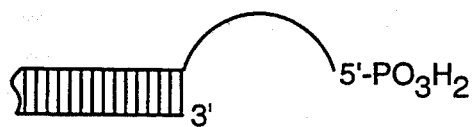
FIG._12
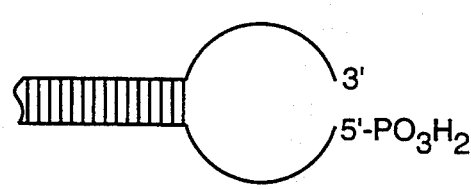
FIG._13

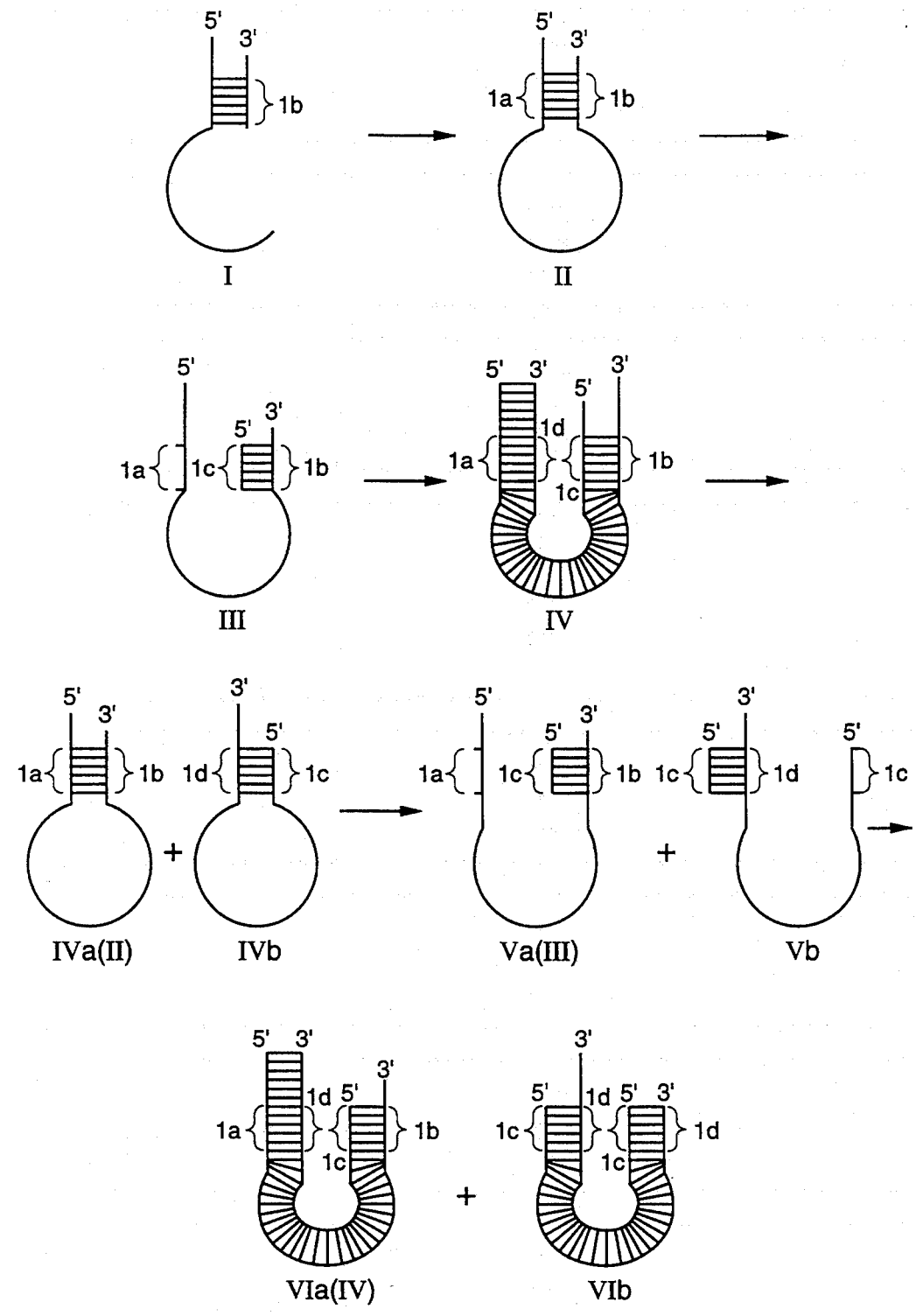
FIG._14

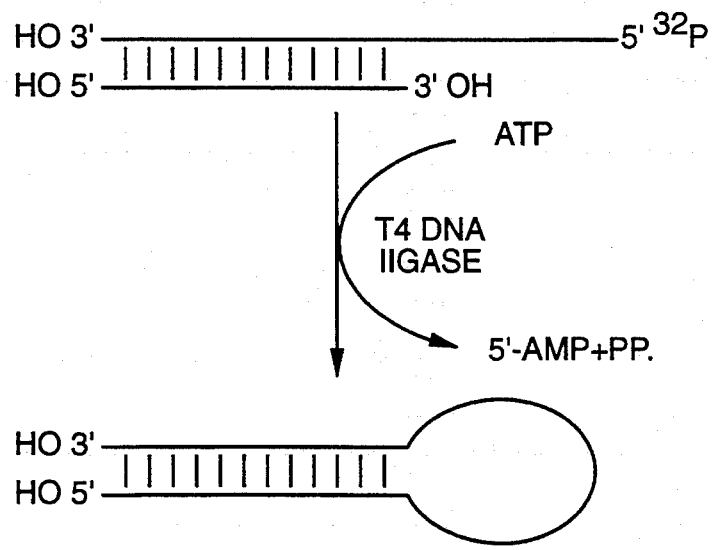
FIG._15
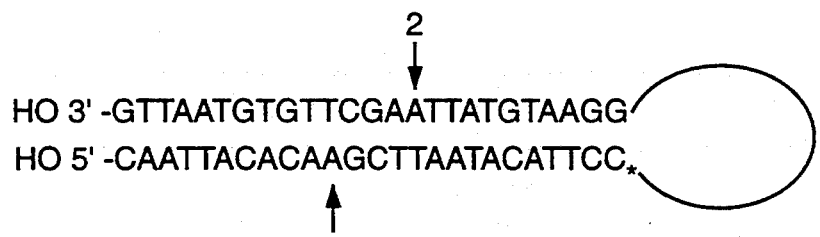
FIG._16

METHOD FOR PRODUCING A POLYNUCLEOTIDE HAVING AN INTRAMOLECULARLY BASE-PAIRED STRUCTURE

BACKGROUND OF THE INVENTION

1. Field of the Invention

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

Current methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the current methods are slow and labor intensive, and nonisotopic labels that are less readily detected than radiolabels are frequently not suitable. A method for increasing the sensitivity to permit the use of simple, rapid, nonisotopic, homogeneous or heterogeneous methods for detecting nucleic acid sequences is therefore desirable.

Recently, a method for the enzymatic amplification of specific segments Of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

2. Description of the Prior Art

A process for amplifying, detecting and/or cloning nucleic acid sequences is disclosed in U.S. Pat. Nos. 4,683,195 and 4,683,202. Sequence polymerization by polymerase chain reaction is described by Saiki, et al., (1986) *Science*, 230: 1350–1354. A method of making an oligonucleotide is described in European Patent Application No. 0194545 A2. Belgian Patent Application No. BE 904402 discloses a mold for making DNA detection probes. Gene amplification in eukaryotic cells is disclosed in U.S. Pat. No. 4,656,134.

Langer, et al., *Proc. Natl. Acad. Sci. USA*, (1981) 78:6633–6637 discloses the enzymatic synthesis of biotin labelled polynucleotides and the use of these materials as novel nucleic acid affinity probes. The detection of vital genomes in cultured cells and paraffin imbedded tissue sections using biotin labelled hybridization probes is discussed by Brigati, et al., *Virology*, (1983) 126: 32–50. U.S. Pat. No. 4,486,539 discloses the detection of microbial nucleic acids by a one step sandwich hybridization test. Sensitive tests for malignancies based on DNA detection is described in U.S. Pat. No. 4,490,472. U.S. Pat. No. 4,480,040 discloses the sensitive and rapid diagnosis of plant viroid diseases and viruses employing radioactively labelled DNA that is complementary to the viroid or to the nucleic acid of the virus being diagnosed. European Patent Application 83106112.2 (Priority U.S. patent application 391,440 filed Jun. 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153. Specific DNA probes in diagnostic microbiology are discussed in U.S. Pat. No. 4,358,535. A method for detection of polymorphic restriction sites and nucleic acid sequences is discussed in European Patent Application No. 0164054 A1. U.S. Pat. No. 4,663,283 describes a method of altering double-stranded DNA.

Genomic amplification with transcript sequencing is discussed by Stoflet, et al., *Science* (198) 259:491. Primer-directed enzymatic amplification of DNA with a thermostable DNA polymerase is described by Saiki, et al., *Science* (1988) 2329:487. U.S. Pat. No. 4,724,202 discloses the use of non-hybridizable nucleic acids for the detection of nucleic acid hybridization. Bugawan, et al., describe the use of non-radioactive oligonucleotide probes to analyze enzymatically amplified DNA for prenatal diagnosis and forensic HLA typing.

Detection and isolation of homologous, repeated and amplified nucleic acid sequences is disclosed in U.S. Pat. No. 4,675,283. A single stranded self-hybridizing nucleic acid probe capable of repeatedly hybridizing to itself or other nucleic acids to form an amplified entity is described in U.S. patent application Ser. No. 888,058, filed Jul. 22, 1986. U.S. Pat. Nos. 4,683,195 and 4,683,202 disclose a homogeneous polynucleotide displacement assay with digestion of the displaced RNA single strand polynucleotide from the reagent complex and amplifying nucleic acid sequences with treatment of separate complementary strands of the nucleic acid with two oligonucleotide primers. European Patent Application No. 0200362 describes a process for amplifying, detecting or cloning nucleic acid sequences and useful in disease diagnosis and in preparation of transformation vectors. A method for simple analysis of relative nucleic acid levels in multiple small samples by cytoplasmic dot hybridization is described in U.S. Pat. No. 4,677,054. A hybridization method of detecting nucleic acid sequences with a probe containing a thionucleotide is described in U.S. Pat. No. 4,647,529.

A simple and efficient enzymatic method for covalent attachment of DNA to cellulose and its application for hybridization-restriction analysis and for in vitro synthesis of DNA probes is described in *Nucleic Acids Research* (1986) 14: 9171-9191. Cleavage of single stranded oligonucleotides by *Eco* RI restriction endonuclease is described in *Nucleic Acid Research* (1987) 15: 709-716.

Exponential Amplification of Recombinant-RNA Hybridization Probes is described by Lizardi, et al. (1988) *Bio/Technology* 6:1197-1202. Fahrlander, et al., discusses Amplifying DNA Probe Signals: A Christmas Tree Approach in *Bio/Technology* (1988) 6:1165-1168.

A nucleic acid hybridization assay employing probes cross-linkable to target sequences is described in U.S. Pat. No. 4,599,303. The method involves the preparation of a specific single stranded ribonucleic acid or deoxyribonucleic acid molecule into which a bifunctional cross-linking molecule has been covalently incorporated. The incorporation is such that the cross-linking molecule retains the capacity to undergo a second reaction with the nucleic acid of the bacterial, vital, or mammalian chromosome, which is the target for the probe such as to form a covalent cross link. Following cross-linking, the uncrossed link probe is separated from covalently cross-linked probe-target complex using one of several procedures which differentiate between single stranded probe and double stranded covalently linked probe-target complex.

A hybridization method and probe for detecting nucleic acid sequences is described in U.S. Pat. No. 4,908,307. An amplified hybridization assay is described in U.S. Pat. No. 4,882,269 wherein a family of signal-generating secondary probes bind to a primary probe that hybridizes to the target sequence of interest.

Detection of target sequences in nucleic acids by hybridization using diagnostic and contiguous probes for diagnosis of genetic abnormality diseases, especially in an automated procedure, is described in European Patent Application No. 0 185 494A2. In the method a sample is hybridized with a probe complementary to a diagnostic portion of the target sequence (the diagnostic probe) and with a probe complementary to a nucleotide sequence contiguous with the diagnostic portion (the contiguous probe) under conditions wherein the diagnostic probe remains bound substantially only to the sample nucleic acid containing the target sequence. The diagnostic probe and contiguous probe are then covalently attached to yield a target probe that is complementary to the target sequence and the probes which are not attached are removed. In a preferred mode, one of the probes is labeled so that the presence or absence of the target sequence can then be tested by melting the sample nucleic acid target probe duplex, eluting the dissociated target probe, and testing for the label.

The above method suffers at least one disadvantage in that contiguous sequences are required. To carry out the method, one must identify the diagnostic sequence and the contiguous sequence and create diagnostic and contiguous probes complementary to the above sequences. If the diagnostic and contiguous sequences are not identified precisely, then the diagnostic and contiguous probes may not hybridize sufficiently and the assay specificity and sensitivity can be lost or substantially decreased.

A DNA amplification and subtraction technique is described in WO89/12695. The method involves isolating genomic or RNA-derived duplex fragments which are unique to one of two fragment mixtures. The fragments in positive-source and negative-source mixtures are separately equipped with end linkers, and each mixture is amplified by successive primed-strand replications, using a single primer which is homologous to the associated linker. The second source linker is biotinylated, and the fragments in this mixture are hybridized in molar excess with the fragments in the positive source mixture. DNA species which are not hybridized with the biotinylated species, i.e., species that are unique to the positive source mixture, are isolated after removal of hybridized species by affinity chromatography. Also disclosed is a method of amplifying a mixture of DNA fragments by repeated linker/primer replication.

U.S. patent applications Ser. Nos. 07/299,282 and 07/399,795, filed Jan. 19, 1989, and Aug. 29, 1989, respectively, describe nucleic acid amplification using a single polynucleotide primer. The disclosures of these two applications are incorporated herein by reference.

T4 DNA ligase has been shown to catalyze the formation of phosphodiester bonds between the 5'-phosphoryl and 3'-hydroxyl end-groups in properly aligned duplex DNA strands (for review, see Richardson (1969) *Ann. Rev Biochem.*, 38: 795-840. The highly specific requirement for a helical DNA substrate, and ATP, was first demonstrated using extracts from *E. coli* infected with bacteriophage T4 (Weiss and Richardson (1967) *Proc Natl. Acad Sci. USA*, 57: 1021-1028; Weiss et al. (1968) *J. Biol. Chem.*, 243: 4543-4555). Since then a variety of DNA substrates have been used to investigate T4 ligase activity. These include hydrogen-bonded circular duplexes of λ DNA, DNA substrates with completely base-paired ends (Sgaramella et al. (1970) *Proc. Natl. Acad. Sci. USA*, 67: 1468-1475; Sgaramella and Khorana (1972) *J. Mol. Biol.*, 72: 493-502; Deugau and van de Sands (1978) *Biochemistry*, 17: 723-729), flush-ended DNA strands generated by restriction endonucleases (Sgaramella and Ehrlich, *Eur. J. Biochem.*, 86: 531-537, and synthetic oligodeoxynucleotides containing an AP (apurinic or apyrimidinic) site, a mispaired base, or a gap at either side of the ligation junction (Goffin et al. (1987) *Nucleic Acids Res.*, 15: 8755-8771; Nilsson and Magnusson, (1982) *ibid.*, 10: 1425-1437; Landegren et al. (1988) *Science*, 241: 1077-1080; Wu and Wallace (1989) *Gene*, 76: 245-254. These rather unconventional ligations take place in the presence of a continuous complementary polynucleotide.

SUMMARY OF THE INVENTION

The invention disclosed herein includes methods and reagents for forming a single stranded polynucleotide having two segments that are non-contiguous and hybridizable with each other. The method finds particular application, for example, in single primer amplification assays.

In one embodiment of the invention a single stranded polynucleotide having two segments that are non-contiguous and hybridizable with each other is produced by a method comprising the step of providing in combination (1) a first polynucleotide sequence having a hydroxyl at its 3' end, (2) a second polynucleotide sequence having a hydroxyl or phosphate group at its 5' end, and (3) a ligase, wherein at least ten consecutive bases of one of the sequences can hybridize to the other of the sequences to form a duplex. The duplex is comprised of a non-hybridized single stranded portion of one of the polynucleotide sequences containing one of the ends and at least five bases. The combination is provided under conditions for forming the duplex and ligating the ends within the duplex.

Another aspect of the invention involves a method of forming a single stranded polynucleotide having two segments that are non-contiguous and hybridizable with each other. The method comprises the step of providing in combination (1) a first polynucleotide sequence, (2) a second polynucleotide sequence, and (3) a ligase, wherein one of the sequences (sequence A) has at least a 10 nucleotide segment hybridizable with a segment of the other sequence (sequence B), and at least one of the 3'-end of sequence A and the 5'-end of sequence B is bound to the corresponding end of the hybridizable segment of the sequence by a single stranded chain of at least five nucleotides. The combination is provided under conditions wherein a phosphodiester is formed between the 5'-end of sequence B and the 3'-end of sequence A.

In another embodiment of the invention a single stranded polydeoxynucleotide having two segments that are non-contiguous and hybridizable with each other is produced by a method comprising the steps of:

combining in a liquid medium (1) a first deoxynucleotide sequence, the 5'-end thereof being separated by at least 5 nucleotides from a segment having at least 10 nucleotides (segment 1A) that is hybridizable with a segment (segment 1B) of a second deoxynucleotide sequence, (2) the second deoxynucleotide sequence and (3) a ligase, wherein the 5'-end of at least one of the deoxynucleotide segments is phosphorylated, and subjecting the medium to conditions under which segments 1A and 1B hybridize with each other and a phosphodiester is formed between the phosphorylated 5'-end of one of the deoxynucleotide sequences and the 3'-end of the other of the deoxynucleotide sequences.

Another aspect of the invention involves a method for detecting the presence of a target polynucleotide sequence in a medium suspected of containing the target polynucleotide sequence. The method comprises the steps of:

combining the medium with (1) a polynucleotide wherein the polynucleotide and the target nucleotide sequence each have a nucleotide segment of at least 10 nucleotides hybridizable with each other, the 5'-end of the polynucleotide or the target nucleotide sequence being phosphorylated and (2) a ligase, subjecting the medium to conditions under which the polynucleotide and the target nucleotide sequence, if present, hybridize to form a duplex having at least one single stranded end and the end becomes ligated to the end of the other polynucleotide member of the duplex and determining whether the polynucleotide and the target nucleotide sequences have become ligated.

The determining may involve forming multiple copies of the target nucleotide sequence ligated to the polynucleotide and detecting the copies. Multiple copies may be formed by single primer amplification or PCR amplification.

Another embodiment of the present invention involves a method for detecting the presence of a polynucleotide analyte in a sample suspected of containing the polynucleotide analyte. The method comprises the steps of:

treating the samples to form a single stranded target nucleotide sequence from the polynucleotide analyte, if present, combining a medium suspected of containing the target nucleotide sequence with (1) a polynucleotide having at least a 10 nucleotide segment hybridizable with a segment of the target nucleotide sequence wherein the 5'-end of the polynucleotide or the 5'-end of the target nucleotide sequence is phosphorylated, and (2) a ligase, subjecting the combination to conditions under which the polynucleotide and the target nucleotide sequence, if present, hybridize to form a duplex having at least one single stranded end and the end is ligated to the other polynucleotide member of the duplex and subjecting a medium suspected of containing said ligated duplex in the presence of nucleoside triphosphates and template dependent polynucleotide polymerase to conditions under which an extension of a polynucleotide primer, at least the 3'-end of which can hybridize with a second flanking sequence non-contiguously bound at the 3'-end of a first flanking sequence of the polynucleotide ligated to the target nucleotide sequence (PLT), is formed, wherein the steps can be performed wholly or partially sequentially or concomitantly, and examining for the presence of extended polynucleotide primer containing a sequence identical to and/or complementary with the PLT.

BRIEF DESCRIPTION OF THE FIGURES

FIG. 1 is an autoradiogram showing the conversion of ON1 (50 mer) into a product 75 bases in length.

FIG. 2 is an autoradiogram comparing product yields when the position of the 5'-phosphoryl end group is either extended or recessed.

FIG. 3 is an autoradiogram showing the restriction digest of the ligated product with Hind III in accordance with the present invention.

FIG. 4 is an autoradiogram of ligation products in accordance with the present invention using ON1 through ON5 as donor sequences.

FIGS. 5–13 are constructs that may be formed into a single stranded polynucleotide in accordance with the present invention.

FIG. 14 is a schematic representation of an embodiment in accordance with the present invention.

FIG. 15 is a synthetic DNA construct referred to in Example 1.

FIG. 16 is the product formed in Example 1.

DESCRIPTION OF THE SPECIFIC EMBODIMENTS

The present method allows for the production of a single stranded polynucleotide having an intramolecularly base-paired structure, i.e., two segments that are non-contiguous and hybridizable with each other. The method comprises the step of providing in combination (1) a first polynucleotide sequence having a hydroxyl at its 3'-end, (2) a second polynucleotide sequence having a hydroxyl or phosphate group at its 5'-end, and (3) a ligase, wherein at least ten consecutive bases of one of the sequences can hybridize to the other of the sequences to form a duplex. The duplex is comprised of a non-hybridized single stranded portion of one of the polynucleotide sequences containing one of the ends and at least five bases. The combination is provided under conditions for forming the duplex and ligating the ends within the duplex.

The present invention in one of its aspects provides for the production of a polynucleotide sequence that can be utilized in the single primer amplification assays described above.

One aspect of the invention involves a method for detecting the presence of a polynucleotide analyte in a sample suspected of containing the polynucleotide analyte. The sample is treated to form a single stranded target nucleotide sequence from the polynucleotide analyte, if the analyte is present. The 5'-end of the target nucleotide sequence is phosphorylated. A medium suspected of containing the target nucleotide sequence is combined with (1) a polynucleotide having at least a 10 nucleotide segment hybridizable with a segment of the target nucleotide sequence, and (2) a ligase. The combination is subjected to conditions under which the polynucleotide and the target nucleotide sequence, if present, hybridize to form a duplex having at least one single stranded end. The end is ligated to the other polynucleotide member of the duplex. Nucleoside triphosphates and template dependent polynucleotide polymerase are added under conditions for forming an extension of a polynucleotide primer at least the 5'-end of which can hybridize with a flanking sequence at the 3'-end of the polynucleotide ligated to the target nucleotide sequence (PLT). An examination is made for the presence of extended polynucleotide primer containing a sequence identical to and/or complementary with the PLT, the presence thereof indicating the presence of the polynucleotide analyte.

Before proceeding further with a description of the specific embodiments of the present invention, a number of terms will be defined.

Polynucleotide analyte—a compound or composition to be measured which is a polymeric nucleotide having in the natural state about 20 to 500,000 or more nucleotides and having in the isolated state about 20 to 50,000 or more nucleotides, usually about 100 to 20,000 nucleotides, more frequently 500 to 10,000 nucleotides. As can be seen, the polynucleotide analyte is frequently fragmented during isolation. The polynucleotide analytes include nucleic acids from any source in purified or unpurified form including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

| Microorganisms of interest include: | |
|---|---|
| Corynebacteria | |
| *Corynebacterium diphtheria* | |
| Pneumococci | |
| *Diplococcus pneumoniae* | |
| Streptococcci | |
| *Streptococcus pyrogenes* | |
| *Streptococcus salivarus* | |
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The colliform |
| *Klebsiella pneumoniae* | bacteria |
| *Salmonella typhosa* | |
| *Salmonella choleraesuis* | The Salmonellae |
| *Salmonella typhisurium* | |
| *Shigella dysenteria* | |
| *Shigella schmitzii* | |
| *Shigella arabinotarda* | The Shigellae |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |
| *Psuedomonas aeruginosa* | |
| *Alcaligenes fascalis* | |
| *Vibrio choleras* | |
| Hemoiphilus-Bordetella group | *Rhizopus oryzae* |
| *Hemophilus influenza, H. ducryi* | *Rhizopus arrhizua* Phycomycetes |
| *Hemophilus hemophilus* | *Rhizopus nigricans* |

TABLE I-continued

| Microorganisms of interest include: | |
|---|---|
| *Hemophilus aegypticus* | *Sporotrichum schenkii* |
| *Hemophilus parainfluenza* | *Flonsecaea pedrosoi* |
| *Bordetella pertussis* | *Fonsecacea compact* |
| Pasteurellae | *Fonsecacea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | Phialophora jeanselmei |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | Herpes simplex |
| *Clostridium histolyticum* | Varicella (Chicken pox) |
| *Clostridium tertium* | Herpes Zoster (Shingles) |
| *Clostridium bifermentans* | Virus B |
| *Clostridium sporogenes* | Cytomegalovirus |
| Mycobacteria | Pox Viruses |
| *Mycobacterium tuberculosis hominis* | Variola (smallpox) |
| *Mycobacterium bovis* | Vaccinia |
| *Mycobacterium avium* | Poxvirus bovis |
| *Mycobacterium leprae* | Paravaccinia |
| *Mycobacterium paratuberculosis* | *Molluscum contagiosum* |
| Actinomycates (fungus-like bacteria) | Picornaviruses |
| *Actinomyces Isaeli* | Poliovirus |
| *Actinomyces bovis* | Coxnackievirus |
| *Actinomyces naeslundii* | Echoviruses |
| *Nocardia asteroides* | Rhinoviruses |
| *Nocardia brasiliensis* | Myxoviruses |
| The Spirochotes | Influenza(A, B, and C) |
| *Treponema pallidum Spirillum minus* | Parainfluenza (1-4) |
| *Treponema pertenue Streptobacillus* | Mumps Virus |
| *monoiliformis* | Newcastle Disease Virus |
| *Treponema carateum* | Measles Virus |
| *Borrelia recurrentis* | Rinderpost Virus |
| *Leptospira icterohemorrhagiae* | Canine Distemper Virus |
| *Leptospira canicola* | Respiratory Syncytial Virus |
| Trypanasomes | Rubella Virus |
| Mycoplasmas | Arboviruses |
| *Mycoplasna pneumoniae* | |
| Other pathogens | Eastern Equine Eucephalitis Virus |
| *Listeria monocytogenes* | Western Equine Eucephalitin Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1-3 |
| | Retroviruses |
| *Rickettsia akari* | Human Immunodeficiency Viruses (HIV) |
| *Rickottsia tsutsugamushi* | Human T-cell Lymphotrophic |
| | Virus I & II (HTLV) |
| *Rickettsia burnetti* | Hepatitis |
| *Rickettsia quintana* | Hepatitis A Virus |
| Chlamydia (unclassifiable parasites | Hepatitis B Virus |
| bacterial/viral) | Hepatitis nonA-nonB Virus |
| Chlamydia agents (naming uncertain) | Tumor Viruses |
| Fungi | Rauscher Leukemia Virus |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidioides brasiliensis* | |
| *Candida albicans* | |

TABLE I-continued

Microorganisms of interest include:

*Aspergillus fumigatus*
*Mucor corymbifer (Abadia corymbifera)* --

The polynucleotide analyte, where appropriate, may be treated to cleave the analyte to obtain a fragment that contains a target polynucleotide sequence, for example, by shearing or by treatment with a restriction endonuclease such as a restriction enzyme or chemical cleavage method, preferably a site specific cleavage method.

For purposes of this invention, the polynucleotide analyte, or the cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90°-100° C. for a period of about 1 to 10 minutes to produce denatured material.

Target polynucleotide sequence—a sequence of nucleotides to be identified, the identity of which is known to an extent sufficient to allow preparation of polynucleotides that will hybridize with at least a portion of such target sequence, usually at least a ten nucleotide segment thereof. The target polynucleotide sequence usually will contain from about 15 to 5000 or more nucleotides, preferably 20 to 1000 nucleotides. The target polynucleotide sequence is frequently a part of the polynucleotide analyte. The target polynucleotide sequence will generally be a fraction of a larger molecule or it may be substantially the entire molecule. The minimum number of nucleotides in the target polynucleotide sequence will be selected to assure that the presence of target polynucleotide sequence in a sample will be a specific indicator of the presence of polynucleotide analyte in a sample. Very roughly, the sequence length will usually be greater than about 1.6 log L nucleotides where L is the number of base pairs in the genome of the biologic source of the sample. The maximum number of nucleotides in the target sequence will normally be governed by the length of the polynucleotide analyte and its tendency to be broken by shearing, by endogenous nucleases or by reagents used to cleave a target sequence from the polynucleotide analyte.

Single stranded polynucleotide—a sequence of nucleotides that is formed as a result of the present invention, usually a single stranded polydeoxynucleotide. It will normally be comprised at least of two segments or flanking sequences that are non-contiguous and hybridizable with each other. It may also contain one or more sequences which, when bound to their complementary sequences, are specific binding sites for receptors such as repressors, restriction enzymes, and the like. The two segments of the single stranded polynucleotide have at least 90% complementary base sequences, usually at least 95% complementary base sequences, often 100% complementary base sequences. The first and second segments or flanking sequences are non-contiguously bound at the 5'- and 3'-ends, respectively, of an intervening nucleotide in the single stranded polynucleotide and each comprises at least ten, preferably at least 15 nucleotides and/or derivatives thereof.

The single stranded polynucleotide will usually contain from 30 to 10,000 nucleotides, preferably 50 to 3,000 nucleotides, more preferably 100 to 500 nucleotides. The single stranded polynucleotide can be RNA or DNA. When the single stranded polynucleotide is hybridized with a complementary strand, it will frequently form inverted repeats.

Polydeoxynucleotide primer—a polydeoxynucleotide containing a sequence at its 3'-end hybridizable with the second segment or flanking sequence at the 3'-end of the single stranded polynucleotide. The number of nucleotides in the polydeoxynucleotide primer that are hybridizable with the second segment or flanking sequence should be such that stringency conditions used to hybridize the polydeoxynucleotide primer will prevent excessive random non-specific hybridization. The number of nucleotides in the polydeoxynucleotide primer may be the same or different than the number of nucleotides in the second segment or flanking sequence, namely, at least ten nucleotides, preferably at least 15 nucleotides and generally from about 10 to 2,000, preferably 20 to 100, nucleotides.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyraxine binding globulin, antibodies, enzymes, Fab fragments, lectins, nucleic acids, repressors, protection enzymes, protein A, complement component Clq, DNA binding proteins or ligands and the like.

Small organic moliecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders suchas silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

The surface will usually be polyfunctional or be capable of being polyfunctionalized or be capable of binding an oligonucleotide or an sbp member through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.* 245,3059 (1970). The length of a linking group to the oligonucleotide or sbp member may vary widely, depending upon the nature of the compound being linked, the effect of the distance between the compound being linked and the particle on the hybridization of the sequences and the like. The oligonucleotide or sbp member will be substantially bound to the outer surface of the particle.

Particles employed as the surface can be fluorescent either directly or by virtue of fluorescent compounds or fluorescers bound to the particle in conventional ways. The fluorescers will usually be dissolved in or bound covalently or non-covalently to the particle and will frequently be substantially uniformly bound through the particle. Fluoresceinated latex particles are taught in U.S. Pat. No. 3,853,987.

Label or reporter group or reporter molecule—A member of the signal producing system that is conjugated to or becomes bound toia probe or a polynucleotide sequence and is capable of being detected directly or, through a specific binding reaction, can produce a detectible signal. Labels include a polydeoxynucleotide primer or specific polynucleotide sequence that can provide a template for amplification or ligation or act as a ligand such as for a repressor protein. In general, any label that is detectable can be used. The label can be isotopic or nonisotopic, usually non-isotopic, and can be a catalyst such as an enzyme, a polynucleotide coding for a catalyst, promotor, dye, fluorescent molecule, chemiluminescer, coenzyme, enzyme substrate, radioactive group, a particle such as latex or carbon particle, metal sol, crystallite, liposome, cell, etc., which may or may not be further labeled with a dye, catalyst or other detectible group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal Producing System—The signal producing system may have one or more components, at least one component being the label or reporter group. The signal producing system generates a signal that relates to the presence or amount of a target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of polynucleotide analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Patent No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and $\beta$-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

The signal producing system can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/ml, and composed of material that can be transparent, partially transparent, or opaque.

The organic particles will normally be comprised of polymers, either addition or condensation polymers, which are readily dispersible in the assay medium. The surface of particles will be adsorptive or functionalizable so as to bind, either directly or indirectly, an oligonucleotide or an sbp member. The nature of particles is described above.

Fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminostilbenes immines, anthracenes, oxacarboxyanine, merocyanine, 3-aminoequilenin, perylene, bis-benzoxazole, bis-p-oxazolyl benzene, 1,2-benzophenazine, retinal, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference.

Additionally, energy absorbent or quenching particles can be employed which are solid insoluble particles of at least about 50 nm in diameter capable of quenching the fluorescence of the fluorescent particle when within the distance resulting from hybridization of a probe with the polynucleotide analyte or from specific binding between members of specific binding pairs. The quenching particle may be the same or different, usually different, from the fluorescent particle. Normally, the quenching particle will provide a substantial quenching at a distance of more than about 50Å, preferably more than about 500Å, more preferably more than about 2000Å, where the distance is measured from the surfaces of the particles.

Many different types of particles may be employed for modulating light emission. Of particular interest are carbon particles, such as charcoal, lamp black, graphite, colloidal carbon and the like. Besides carbon particles metal sols may also find use, particularly of the noble metals, gold, silver, and platinum. Other metal-derived particles may include metal sulfides, such as lead, silver or copper sulfides or metal oxides, such as iron or copper oxide.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino analog of the above compound. Other members of the family include the 5-amino-6,7,8-trimethoxy- and the dimethylamine-[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino- and para-methoxysubstituents. Chemiluminescence may also be obtained with oxilates, usually oxalyl, active esters, e.g., p-nitrophenyl and a peroxide, e.g., hydrogen peroxide, under basic conditions. Alternatively, luciferins may be used in conjunction with luciferase or lucigenins.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

Nucleoside triphosphates—a nucleoside having a 5' triphosphate substituent, preferably a deoxynucleoside triphosphate. The natural nucleosides are pentose sugar derivatives of nitrogenous bases of either purine or pyrimidine derivation, covalently bonded to the 1'-carbon of the pentose sugar. The purine bases include adenine(A), guanine(G), inosine, and derivatives and analogs thereof. The pyrimidine bases include cytosine (C), thymine (T), uracil (U), and derivatives and analogs thereof. Unnatural nucleoside triphosphates employ analogs of purines and pyrimidines that are incorporated into polynucleotides by nucleotide polymerase catalysis.

The derivatives and analogs are exemplified by those that are recognized and polymerized in a similar manner to the underivitized nucleoside triphosphates. Examples of such derivatives or analogs by way of illustration and not limitation are those which are modified with a reporter group, biotinylated, amine modified, radiolabeled, alkylated, and the like and also include thiophosphate, phosphite, ring atom modified derivatives, and the like. The reporter group can be a fluorescent group such as fluoroscein, a chemiluminescent group such as luminol, a terbium chelator such as N-(hydroxyethyl) ethylenediaminetriacetic acid that is capable of detection by delayed fluorescence, and the like.

Polydeoxynucleotide polymerass—a catalyst, usually an enzyme, for forming an extension of the polydeoxynucleotide primer along a DNA or RNA template comprising the single stranded polynucleotide, a portion of which is hybridized to the primer. The polydeoxynucleotide polymerase is a template dependent polydeoxynucleotide polymerase and utilizes the deoxynucleoside triphosphates as building blocks for extending the 3'-end of the polynucleotide primer to provide a sequence complementary with the single stranded polynucleotide. Usually, the catalysts are enzymes, such as DNA polymerases such as, for example, prokaryotic DNA polymerase (I, II, or III), T4 DNA polymerase, T7 DNA polymerase, Klenow fragment, reverse transcriptase, and the like derived from any source such as cells, bacteria, such as *E. coli*, plants, animals, virus, thermophilic bacteria, and so forth.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the stringency which include temperature, solvent ratios, salt concentrations, pH, and the like.

First polynucleotide sequence—a sequence of nucleotides having hydroxyl at its 3'-end at least a portion of such sequence, preferably at least ten consecutive nucleotides thereof, capable of hybridizing with a portion of a second nucleotide sequence by virtue of being partially or completely, usually completely, complementary to a region of the second nucleotide sequence such that the first polynucleotide sequence will become bound to such region of the second nucleotide sequence. The first polynucleotide sequence may thus contain additional sequences of nucleotides located at either end of the sequence capable of hybridizing with the second nucleotide sequence.

The major criteria for choosing the first polynucleotide sequence are: (1) The binding sequence for the portion of the second nucleotide sequence should be reliable, that is, it should be closely or exactly complementary with at least a portion of the second nucleotide sequence and should be of sufficient length to provide stable and specific binding. (2) The 3'-end must form, or be capable of forming, a free 3'-hydroxyl group. The minimum binding sequence will usually be at least 10, preferably at least 15, nucleotides in length. Additional sequences, located between the 3'-end or the 5'-end and the binding sequence may be present where the first polynucleotide sequence is a target polynucleotide sequence to provide, for example, for receptor binding sites to permit detection of the amplified product. In general, the first poynucleotide sequence will be about 30 to 5,000 nucleotides, more frequently 40 to 1,000 nucleotides in length. The combined length of the hybridizing portion of the first and second polynucleotide sequences is at least about 20 nucleotides, preferably about 40 to 2,000 nucleotides, in length.

Second polynucleotide sequence—a sequence of nucleotides having a hydroxyl or a phosphate at its 5'-end, at least a portion of which is capable of hybridizing with a portion of the first nucleotide sequence. The second polynucleotide sequence has a sequence at least ten consecutive nucleotides that is at least 90% complementary, usually completely complementary to a portion of the first polynucleotide sequence. Thus, the first and second polynucleotide sequences each have a polynucleotide sequence that is at least partially complementary to a sequence in the other. The second polynucleotide sequence may contain additional receptor binding or spacer sequences located between the binding sequence and the 3'- or 5'-end and may be a target polynucleotide sequence.

Non-contiguous—sequences are non-contiguous, there being at least one nucleotide present in the single stranded polynucleotide between the two segments.

Contiguous—sequences are considered to be contiguous when there are no nucleotides between the two segments.

Copy—means a sequence that is a direct copy of a single stranded polynucleotide as differentiated from a sequence that is complementary to the sequence of such single stranded polynucleotide. In single primer amplification conducted following the present invention a complementary sequence of a single stranded polynucleotide is produced initially as the result of the extension of the polydeoxynucleotide primer along a single stranded polynucleotide and a sequence that is a direct copy of the single stranded polynucleotide is subsequently obtained by extension of the polydeoxynucleotide along the aforementioned complementary sequence.

Ligase—Any catalyst, usually an enzyme, capable of catalyzing the reaction of the polynucleotide 3'-hydroxyl group with a 5'-hydroxyl group or its phosphate to form a phosphodiester. Examples, by way of illustration and not limitation, of such enzymes are ligases from any source such as *E. coli* bacterial ligase, T4 phage DNA ligase, mammalian DNA ligase, RNA ligase, and the like.

Covalently attaching—forming a chemical bond between the first polynucleotide sequence and the second polynucleotide sequence. Covalent attachment is usually achieved enzymatically by utilizing a ligase.

Means for extending a primer—a polydeoxynucleotide primer having an extendable 3'-terminus can be extended by combining the primer hybridized to the polynucleotide sequence ligated to a target nucleotide sequence with a polydeoxynucleotide polymerase and nucleoside triphosphates under conditions for extending the primer.

One embodiment of the present invention concerns a method of forming a single stranded polynucleotide having two segments that are non-contiguous and hybridizable with each other. The method comprises providing in combination (1) a first polynucleotide sequence having a hydroxyl at its 3'-end, (2) a second polynucleotide sequence having a hydroxyl or phosphate group at its 5'-end, and (3) a ligase, wherein at least ten consecutive bases of one of the sequences can hybridize to the other of the sequences to form a duplex. The duplex is comprised of a non-hybridized single stranded portion of one of said polynucleotide sequences containing one of the ends and at least five bases. The combination is provided under conditions for forming the duplex and ligating the ends within the duplex.

Preferably, the second polynucleotide sequence has a phosphate group at its 5'-end. It is also desirable that the 5'-end of the second sequence be hybridized in the duplex. In other words, it is preferable that the second polynucleotide sequence have no nucleotides between its 5'-end and the sequence that binds to the first polynucleotide sequence. More preferably, the 5'-end of the second polynucleotide sequence has a phosphate group. It follows then that it is preferable that the first polynucleotide have, when bound to the second polynucleotide, a non-hybridized single stranded portion of at least 5 bases at its 3'-end.

In another aspect of this embodiment the duplex is comprised of a non-hybridized single stranded portion of each of the polynucleotide sequences, one containing a 3'-end and one containing a 5'-end, and at least five bases and wherein the 5'-end has a phosphate group.

Another embodiment of the present invention is a method of forming a single stranded polynucleotide having two segments that are non-contiguous and hybridizable with each other. The method comprises providing in combination (1) a first polynucleotide sequence, (2) a second polynucleotide sequence, and (3) a ligase, wherein one of the sequences (sequence A) has at least a 10 nucleotide segment hybridizable with a segment of the other sequence (sequence B), and at least one of the 3'-end of sequence A and the 5'-end of sequence B is bound to the corresponding end of the hybridizable segment of the sequence by a single stranded chain of at least five nucleotides. The combination is provided under conditions wherein a phosphodiester is formed between the 5'-end of sequence B and the 3'-end of sequence A. Preferably, the 5'-end of sequence B is phosphorylated and more preferably, the nucleotide at the 5'-end that is phosphorylated is cytosine (C). The single stranded polynucleotide can preferably be from 30–1000 nucleotides. The 3'-end of sequence A or the 5'-end of sequence B can be part of the hybridizable segment.

Preferably, the ligase is T4 DNA ligase. The hybridizable nucleotide segments preferably contain at least a 10 nucleotides complementary to each other. In a preferred aspect the ligase is present in a concentration substantially in excess relative to the concentration of said first and second sequences.

The following are examples (see FIGS. 5–8), by way of illustration and not limitation, of constructs that may be formed into a single stranded polynucleotide in accordance with the present invention: The particular constructs depicted in FIGS. 9–13 are preferable (in descending order FIG. 9 to FIG. 13).

The non-hybridized single stranded sequences in the duplexes shown above are preferably 5 to 100 nucleotides in length. Preferably, the 5' base is cytosine (C) when it is part of the hybridized sequence wherein yields of ligated duplex are maximized. It should be apparent to one skilled in the art that either one or the other of the first and second polynucleotide sequences can be a target polynucleotide sequence or a polynucleotide probe.

The present invention demonstrates an unexpected and novel activity of T4 DNA ligase. The activity allows target specific ligation of a DNA oligomer containing a 5' phosphorylated terminus to a target DNA strand containing a 3' hydroxy terminus, yielding a stem-loop structure. Amplification of the stem-loop structure by single primer amplification, as described in U.S. patent applications Ser. Nos. 07/299,282 and 07/399,795, provides for amplification of a portion of the target sequence.

Until the present invention, those skilled in the art believed that T4 DNA ligase was incapable of ligating single-stranded DNA molecules to one another (see Methods in Enzymology, Vol. 68 (1979), pages 50–71).

The present invention demonstrates that partially base-paired oligodeoxynucleotides are substrates for a ligase and thus can be ligated together. Thus, the present invention provides a novel method for preparing molecules useful in single primer amplification.

Another embodiment for forming a single stranded polynucleotide having two segments that are non-contiguous and hybridizable with each other comprises combining in a liquid medium (1) a first nucleotide sequence, the 5'-end thereof being separated by at least 5 nucleotides from a segment having at least 10 nucleotides (segment A) that is hybridizable with a segment (segment 1B) of a second nucleotide sequence, (2) The second nucleotide sequence and (3) a ligase, wherein the 5'-end of at least one of the nucleotide segments is phosphorylated, and subjecting the medium to conditions under which segments 1A and 1B hybridize with each other and a phosphodiester is formed between the phosphorylated 5'-end of one of the nucleotide sequences and the 3'-end of the other of the nucleotide sequences.

The conditions utilized for hybridization and for forming the phosphodiester bond generally involve heating the combination to a temperature of about 35° to 95° C., preferably 55° to 65° C., for a period of 1 to 60 mins., preferably 1 to 5 mins. Preferably, the first combined medium, usually aqueous buffered, is heated to hybridize the sequences. Then, the combination is cooled to 20° to 50° C., preferably 20° to 30° C., for about 1 to 30 mins. Ligase is then added to the medium. However, the reaction can be conducted by combining the first and second polynucleotide sequences and the ligase in the medium and proceeding as described above. The ligase is present in an amount sufficient to form the desired phosphodiester bond. Generally, the ligase is present in a concentration of about 500 to 100-fold excess relative to that of the first and second sequences. Preferably, the ligase is present in excess relative to the concentration of the first and second sequences, usually 200 to 100-fold excess. The time period for formation of the phosphodiester bond is about 1 hour to 24 hours, preferably 1 to 2 hours at a temperature of about 37° to 20° C., preferably 25° to 20° C.

Another embodiment of the present invention concerns a method for detecting the presence of a target polynucleotide sequence in a medium suspected of containing the target polynucleotide sequence. The medium is combined with (1) a polynucleotide wherein the polynucleotide and the target nucleotide sequence each have a nucleotide segment of at least 10 nucleotides hybridizable with each other, the 5'-end of the polynucleotide or the target nucleotide sequence being phosphorylated and (2) a ligase. The medium is subjected to conditions under which the polynucleotide and the target nucleotide sequence, if present, hybridize to form a duplex having at least one single stranded end and the end becomes ligated to the end of the other polynucleotide member of the duplex. Next, a determination is made as to whether the polynucleotide and the target nucleotide sequences have become ligated. The conditions for ligating are described above for the formation of a phosphodiester bond.

The determining step can involve forming multiple copies of the target nucleotide sequence ligated to the polynucleotide (the ligated molecule referred to as TLP) and detecting the TLP. The multiple copies can be prepared, for example, by single primer amplification.

In the latter amplification multiple copies are formed by incubating the assay medium under conditions for either wholly or partially sequentially or concomitantly (1) hybridizing a single stranded polydeoxynucleotide primer at its 3'-end to the flanking sequence at the 3'-end of the TLP, (2) extending the polydeoxynucleotide primer in the presence of nucleotide triphosphates and a polynucleotide polymerase to provide a first extended polydeoxynucleotide primer, (3) dissociating the first extended polydeoxynucleotide primer and the TLP, (4) hybridizing the first extended polynucleotide primer with the polynucleotide primer, (5) extending the polydeoxynucleotide primer along the first extended polydeoxynucleotide primer to provide a second extended polydeoxynucleotide primer, (6) dissociating the second extended polydeoxynucleotide primer from the first extended polydeoxynucleotide primer, and (7) repeating steps (4)–(6) above.

The polynucleotide primer is preferably 10 to 100 nucleotides in length. Preferably, the 5'-end of the target nucleotide sequence is phosphorylated. The 5'-end of the target nucleotide sequence preferably is separated from the segment by 10 to 1000 nucleotides. In a preferred embodiment the nucleotide at the 5'-end that is phosphorylated is cytosine (C). FIG. 14 provides an example, by way of illustration and not limitation, of the above embodiment.

Referring to FIG. 14, Structure I depicts a Polynucleotide and a target nucleotide hybridized at segments 1a and 1b. For purposes of this example the strand containing sequence 1a is designated the target nucleotide sequence, which is phosphorylated at its 5'-end. The sequence containing 1a is then referred to as the polynucleotide, which has a non-hybridized nucleotide sequence at its 3'-end. It is to be understood that either strand may be the target nucleotide sequence depending on the nature of the assay to be conducted and the analyte to be determined. The hybridized molecules can be combined with a ligase to form a phosphodiester bond and yield ligated molecule II. Hybridization of polynucleotide primer 1c with molecule II yields molecule III. Primer 1c has substantially the same or a similar polynucleotide sequence as sequence 1a. In the presence of DNA polymerase and nucleoside triphosphates primer 1c is extended along molecule II to yield molecule IV. Dissociation of molecule IV yields single stranded IVa and IVb. Molecule IVa is the unchanged molecule II and has complementary sequences 1a and 1b and molecule IVb has complementary sequences 1c and 1d. As is evident 1c corresponds to 1a, and 1d corresponds to 1b. Polynucleotide primer 1c can be hybridized to region 1b of IVa and to region 1d of IVb to yield molecules Va (III) and Vb, respectively. Extension of primer 1c along Va and Vb under conditions described above yields molecules VIa (IV) and VIb, respectively. Molecules VIa and VIb can be dissociated to single stranded polynucleotides, which can then hybridize with primer 1c and the chain extension can be repeated. In this way multiple copies of the initial single stranded polynucleotide encompassing the sequence between the sequences 1a and 1b of molecule II, and a sequence complementary thereto, can be obtained.

In carrying out the method of forming the single stranded polynucleotide and amplification an aqueous medium will be employed. Other polar cosolvents may also be employed, usually oxygenated organic solvents of from 1–6, more usually from 1–4, carbon atoms, including alcohols, ethers and the like. Usually these cosolvents will be present in less than about 70 weight percent, more usually in less than about 30 weight percent.

The pH for the medium will usually be in the range of about 4.5 to 9.5, more usually in the range of about 5.5–8.5, and preferably in the range of about 6–8. The pH and temperature are chosen and varied, as the case may be, so as to provide for efficient ligation and either simultaneous or sequential dissociation of any internally hybridized sequences in the first and second polynucleotide sequences or the single stranded polynucleotide sequence, hybridization of the polydeoxynucleotide primer with the single stranded polynucleotide, extension of the primer, dissociation of the extended primer, hybridization of extended primer with primer, extension of the so-hybridized primer, and dissociation of extended primer. In some instances, a compromise will be made between these considerations depending on whether the above steps are performed sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method. Desirably constant temperatures during the period for conducting the method will be used but frequently the medium will be cycled between two or three temperatures. When constant, the temperature will be near the melting temperature of the complex of the single stranded polynucleotide and the extended polynucleotide primer. The temperatures for the method will generally range from about 10° to 100° C., more usually from about 20° to 95° C., preferably 35° to 70° C. However, the temperature can be varied depending on whether the above steps are carried out sequentially or simultaneously. For example, relatively low temperatures of from about 20° to 40° C. can be employed for the extension steps, while denaturation and hybridization can be carried out at a temperature of from about 50° to 95° C.

The time period for carrying out the method of the invention will generally be long enough to achieve a desired number of copies of the single stranded polynucleotide or a sequence complementary thereto. This, in turn, depends on the purpose for which the amplification is conducted, such as, for example, an assay for a polynucleotide analyte. Generally, the time period for conducting the method will be from about 1 to 10 minutes per cycle and any number of cycles can be used from 1 to as high as 200 or more, usually 1 to 80, frequently 20–80. As a matter of convenience it will usually be desirable to minimize the time period and the number of cycles. In general, the time period for a given degree of amplification can be shortened, for example, by selecting concentrations of nucleoside triphosphates sufficient to saturate the polydeoxynucleotide polymerase and by increasing the concentrations of polydeoxynucleotide polymerase and polydeoxynucleotide primer.

The amount of the single stranded polynucleotide which is to be copied can be as low as one or two molecules in a sample but will generally vary from about $10^2$ to $10^{10}$ more usually from about $10^3$ to $10^8$ molecules in a sample. The amount of the polydeoxynucleotide primer will be at least as great as the number of copies desired and will usually be $10^{-15}$ to $10^{-9}$ moles per sample, where the sample is 10–1,000 μL. Usually, the primer will be present in at least $10^{-12}$ M, preferably $10^{-10}$ M, and more preferably at least about $10^{-8}$ M. Preferably, the concentration of the polydeoxynucleotide primer is substantially in excess over, preferably at least 100 times greater than, the concentration of the single stranded polynucleotide.

The final concentration of each of the reagents will normally be determined empirically to optimize the number of the copies of the target sequence.

The concentration of the deoxynucleoside triphosphates in the medium can vary widely; preferably, these reagents are present in an excess amount. The deoxynucleoside triphosphates will usually be present in $10^{-6}$ to $10^{-2}$M, preferably $10^{-5}$ to $10^{-3}$M.

The concentration of the template-dependent polydeoxynucleotide polymerase will usually be determined empirically. Preferably, a concentration will be used that is sufficient such that further increase in the concentration will not decrease the time for the amplification by over 5-fold, preferably 2-fold. The primary limiting factor generally is the cost of the reagent.

The order of combining of the various reagents to form the combination may vary. Generally, the target nucleotide sequence is obtained from a sample containing such sequence or a polynucleotide analyte that has been treated to obtain such sequence. The target nucleotide sequence can be obtained from a sample by appropriate cutting of the polynucleotide analyte. Methods for cutting DNA and the like are well-known in the art and include contacting the sample with an enzyme such as a restriction enzyme, endonuclease, S1 nuclease, a sequence specific DNA binding protein with attached DNA cleaving moieties, and the like. Generally, the target nucleotide sequence and the polynucleotide are combined and hybridized. Ligase is then added and the combination treated as described above to form a phosphodiester bond. The single stranded polynucleotide with first and second hybridized segments may be combined with a pre-prepared combination of polydeoxynucleotide primer, deoxynucleoside triphosphates, and template-dependent polydeoxynucleotide polymerase. However, simultaneous addition of the above, as well as other step-wise or sequential orders of addition, may be employed.

The concentration and order of addition of reagents and conditions for the method are governed generally by the desire to maximize the number of copies of the single stranded polynucleotide sequence and the rate at which such copies are formed. Generally, it is desirable to increase the number of copies of the single stranded polynucleotide sequence by at least a factor of $10^2$, preferably a factor of $10^4$ more preferably $10^6$ or more.

The present invention has particular application to the determination or detection of a polynucleotide analyte in a sample. In general, the method comprises forming as a result of the presence of an analyte a single stranded target nucleotide sequence. This may be achieved as described above. Next, the target nucleotide sequence is combined with (1) a polydeoxynucleotide having at least a 10 nucleotide segment hybridizable with a segment of the target nucleotide sequence wherein the 5'-end of the polydeoxynucleotide or the 5'-end of the target nucleotide sequence is phosphorylated, and (2) a ligase. The combination is subjected to conditions under which the polydeoxynucleotide and the target nucleotide sequence, if present, hybridize to form a duplex having at least one single stranded end and the end is ligated to the other polynucleotide member of the duplex. A medium suspected of containing the ligated duplex is combined with nucleoside triphosphates and template dependent polydeoxynucleotide polymerase under conditions under which is formed an extension of a polydeoxynucleotide primer, at least the 5'-end of which can hybridize with a flanking sequence at the 3'-end of the polynucleotide ligated to the target nucleotide sequence (the ligated molecule referred to as PLT). Next, the medium is examined for the presence of extended polydeoxynucleotide primer containing a sequence identical to and/or complementary with the PLT.

The order of combining of the various reagents to form the combinations referred to above may vary and can be concomitant or simultaneous or wholly or partially sequential. Generally, a sample containing a polynucleotide analyte is obtained and treated to yield a target nucleotide sequence. The target nucleotide sequence can be combined with the appropriate polynucleotide and the two hybridized. Next, a ligase is added to covalently link the polynucleotide and the target nucleotide sequence. The resulting molecule may be combined with a pre-prepared combination of first and second polynucleotide probes, nucleoside triphosphates, and polynucleotide polymerase. However, simultaneous addition of the above, as well as other step-wise or sequential orders of addition, may be employed. The concentration and order of addition of reagents and conditions for the method are governed generally by the desire to optimize hybridization of all of the target polynucleotide sequence with the polynucleotide and ligation of the so-hybridized molecules.

Following ligation of the target nucleotide sequence and the polynucleotide when these molecules are hybridized, the hybridized molecule is dissociated. Multiple copies of the single stranded polynucleotide resulting from the ligated molecules are then prepared. In one approach multiple copies of the single stranded polynucleotide are obtained by the procedures described above using a single polynucleotide primer. In another approach multiple copies of the single stranded polynucleotide are obtained by using the double primer technique described in U.S. Pat. Nos. 4,683,195 and 4,683,202, the disclosures of which are incorporated herein by reference. In still another approach amplification can be achieved as described in U.S. patent application Ser. No. 076,807 filed Jul. 23, 1987, now U.S. Pat. No. 4,994,368 the disclosure of which is incorporated herein reference. It will be appreciated by those skilled in the art that other methods of forming multiple copies can be used in the present invention for detection of an analyte.

Detection of extended polydeoxynucleotide primer containing a sequence identical to and/or complementary to PLT indicates the presence of the polynucleotide analyte in the sample.

In carrying out the method of the invention as applied to the detection of a polynucleotide analyte, an aqueous medium is employed, which may further contain other polar solvents as described above. The pH, temperature, time, and concentration of reagents generally will be those described above for the formation of multiple copies of a single stranded polynucleotide.

The pH for the medium will usually be in the range of about 4.5 to 9.5, more usually in the range of about 5.5-8.5, and preferably in the range of about 6-8.

The temperatures for the method will generally range from about 20° to 90° C., more usually from about 30° to 70° C. preferably 37° to 50° C.

Generally, the time period for conducting the method will be from about 5 to 200 min. As a matter of convenience, it will usually be desirable to minimize the time period.

The concentration of the target polynucleotide analyte can be as low as possibly one molecule, preferably at least $10^{-21}$M in a sample but will generally vary from about $10^{-14}$M to $10^{-19}$M, more usually from about $10^{-16}$ to $10^{-19}$M. The concentration of the first and second polynucleotide probes and the deoxynucleoside triphosphates in the medium can vary widely. Preferably, these reagents will be present in large molar excess over the amount of target analyte expected. The deoxynucleoside triphosphates will usually be present in $10^{-6}$ to $10^{-2}$M, preferably $10^{-5}$ to $10^{-3}$M. The second polynucleotide probe, as well as the first polynucleotide probe, will usually be present in at least $10^{-12}$M, preferably $10^{-10}$M, more preferably at least about $10^{-8}$M.

The concentration of the polymerase and any cofactors in the medium can also vary substantially. These reagents may be present in as low as $10^{-12}$M but may be present in a concentration at least as high or higher than the concentration of the first and second nucleotide probes.

While the concentrations of the various reagents will generally be determined by the concentration range of interest of the polynucleotide analyte, the final concentration of each of the reagents will normally be determined empirically to optimize the sensitivity of the assay over the range of interest. The concentration of the other reagents in an assay generally will be determined following the same principles as set forth above for the amplification method. The primary consideration is that a sufficient number of copies of PLT be produced in relation to the polynucleotide analyte sequence so that such copies can be readily detected and provide an accurate determination of the polynucleotide analyte. The copies of PLT can be detected in numerous ways. For example, in the present method, some of the molecules of the polynucleotide primer can be labeled with a ligand (B) and other of the molecules of the polynucleotide primer can be labeled with a detectable label (F).

In another example the ligand can be a small organic molecule, a polynucleotide sequence, a protein, or the like. Upon amplification, a mixture of duplexes is obtained, some having ligand at both ends, some having detectable label at both ends, and some having ligand at one end and detectable label at the other. The ratios of the products can be modified by varying the ratio of the two differently labeled primers. The duplexes can be detected by causing the molecule to bind to a surface to which is bound a receptor for the ligand. Duplexes containing the two primer labels that are shorter than the PLT copies can be prevented from binding by using conditions that are stringent enough to dissociate only these shorter duplexes. After removal of unbound material, the support is examined for the presence of a detectable label. The presence thereof indicating the presence of polynucleotide analyte in the sample.

In another approach, the internally hybridizable sequences can be selected because a synthetic or natural receptor exists that can bind to the hybridized sequences. The sequences will usually be introduced by including them between the target nucleotide sequence binding sequence and that of the polynucleotide. Alternatively, they can be introduced as labels at the 5'-end of a portion of the polynucleotide primer molecules. The tetracycline repressor is such a receptor. This protein binds to the tetracycline operator and the hybridized sequences can be selected to comprise some or all of this operator. The repressor is bound to a solid support and used to absorb and concentrate the amplification product from the amplification reaction solution. The bound product can then be detected by staining with a dye such as acridinium orange, by changes in a physical property of the adsorbent such as electrical properties, optical properties, acoustic wave modulation, and the like, or by detecting the presence of a label bound to another portion of the polynucleotide primer molecules.

Other operator-repressor pairs can be used including, for example, the 1ac repressor and operator which have been used as a ligand and receptor for capture of DNA duplexes and the tryptophane repressor and operator.

In another approach bromodeoxyuridine can be incorporated into a portion of the polynucleotide primer molecules and antibodies to bromodeoxyuridine can be employed. Detection of the bound sequence can be accomplished by any of the above methods.

In a preferable approach for detection of the PLT copies, the copies are simultaneously or sequentially denatured by heating or use of denaturing solvents and solutes and caused to bind to a support by, for example, one of the above methods. The support is then contacted with a probe comprised of a nucleic acid sequence and a label or receptor binding site. The nucleic acid sequence is complementary to at least the portion of the PLT copies. The presence of the PLT copy is then indicated by the presence of the label or receptor binding site on the support.

Other assay formats and detection formats are disclosed in U.S. patent applications Ser. Nos. 07/229,282 and 07/399,795 filed Jan. 19, 1989, and Aug. 29, 1989, respectively, which have been incorporated herein by reference.

Any standard method for specifically detecting double strand nucleic acid sequences can be used.

One method for detecting nucleic acids is to employ nucleic acid probes. This method generally involves immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about ten minutes to forty-eight hours. After the above time period, the solid support is washed several times to remove unbound probe and the hybridized material is detected by autoradiography or spectroscopic methods.

One method utilizing probes is described in U.S. patent application Ser. No. 773,386, filed Sep. 6, 1985, the disclosure of which is incorporated herein by reference. The method comprises combining in an assay medium the sample and first and second polynucleotide reagents complementary to the nucleic acid fragment. Each of the first and second reagents hybridize with a different region of nucleic acid fragment. The first reagent contains means for tendering the first reagent non-covalently polymerizable. The second reagent contains means for rendering the second reagent detectable. The sample and the first and second reagents are combined in the assay medium under conditions for polymerizing the first reagent wherein the second reagent becomes bound to the polymerized first reagent only when the DNA fragment is present in the sample. A determination is then made as to whether the second reagent has become bound to the polymerized first reagent.

In order to separate the PLT copies from other components in an assay mixture containing a sample it can be desirable, and indeed preferable in some circumstances, that the polynucleotide or polynucleotide primer has, or is capable of having, means for immobilizing the sequence. Generally, this means for immobilizing involves a support. The sequence in question can be treated to bind the sequence to a support prior to the use of this sequence in the method of the present invention. Numerous methods are known for binding nucleotide sequences to solid supports. For example see T. Goldkorn et al., *Nucleic Acids Research* (1986) 14:9171–9191 and the references contained therein. Generally, the procedures for attaching the nucleotide sequence to supports involve chemical modifications of some of the nucleotides in the sequence whereby the sequence can then be attached to the support. Preferably, the bond between the support and the nucleotide sequence will be covalent, more preferably involving a linking group between the nucleotide sequence the support. For example, the support can be treated to introduce maleimide groups and the nucleotide sequence can be treated to introduce a thiol group. The thiol group is reactive with the activated olefin of the maleimide group and in such a fashion the nucleotide sequence can be covalently bound to the support. Examples of other such linking groups are cellulose derivatized with diazobenzyloxymethyl groups as described by Noyes, B. E. and Start, G. R., *Cell* 5, 301 (1975) and Alwine, J. C., et al., *Proc. Natl. Acad. Sci.*, U.S.A. 74, 5350 (1977), and cellulose derivatized with o-aminophenylthioether, such as described by Seed, B., *Nucleic Acids Res.*, 10, 1799 (1982).

If the nucleotide sequence is not initially bound to a support, it may be desirable that one of the two sequences become bound to a support at some time during the method of the invention, preferably, prior to the detection of the PLT copies. Accordingly, the support and one of the nucleotide sequences must contain reactive groups which can provide a linkage between the support and the nucleotide sequence. The nature of the reactive groups will be such as to be compatible with the method of the present invention.

One such system is that described above where the support would contain maleimide groups and the nucleotide sequence would contain a thiol group. In another embodiment the nucleotide sequence and the support can contain complementary specific binding pair members such as biotin-avidin and the like. Thus, the method of the present invention can be run in solution and at the appropriate time the support can be introduced whereupon the complementary sbp members will bind. After the support is washed, to remove unbound material, further reactions or determinations can be carried out.

Other examples of such systems are repressor-operator interactions where one of the nucleotide sequences is captured at the solid surface by its sequence specific interaction with a specific repressor or modulator protein immobilized on the solid surface. An advantage of this embodiment of the capture phase is that in some cases release of the operator DNA from the repressor can be accomplished by treating the complex with an inducer molecule. For example, the tetracycline repressor may be immobilized on a solid surface so that an operator sequence present on one or the other of the nucleotide sequences is specifically captured and retained when the solution is contacted to the surface. The surface may then be washed to eliminate any non-specific binding and finally the operator containing nucleotide may be released from the surface by contacting the repressor-operator complex bound at the surface with an inducer molecule (tetracycline or one of its active analogs in this case).

The inducer molecule may be the "natural inducer" in the sense that it is structurally identical with the molecule in nature that causes dissociation of the biological/regulatory repressor-operator complex or it may be a synthetic analog of the natural inducer with similar or enhanced binding and complex dissociation activity. Examples of the above include the tetracycline repressor-operator interaction and its dissociation by tetracycline such as described by Hillen, W., et al., *J. Mol. Biol.*, 169, 707–721 (1983) and Klock, G., *J. Bact.*, 16, 326–332 (1985).

In the situation where the nucleotide sequence is covalently attached to the support, it may be desirable to remove the attached sequence from the support, such as, for example, in order to amplify or clone the sequence. In this situation it is desirable to introduce a cleavable group between the nucleotide sequence and the support. Exemplary of such cleavable groups are pyrophosphate linkages, disulfide linkages and restriction enzyme cleavage sites.

The support may be removed from the medium, washed free of unbound material, and then examined for the presence of PLT copies, for example, by detecting the presence of a label or a reporter group. Generally, this examination involves contacting the support with the remaining members of a signal producing system in order to produce a signal in relation to the presence of the target nucleotide sequence in the sample.

In the present invention a support may be washed under conditions that would normally be more vigorous than those used when hybridization is carried out without covalent attachment. Frequently, the washing conditions will completely disassociate duplexes bound to the support. These conditions include solutions containing kaotropic agents such as urea either alone or in combination with other denaturants such as formamide used either at ambient or elevated temperature. The covalent attachment between the target polynucleotide sequence and the polynucleotide and the bonding of one of the probes to a surface, however, will be unaffected. Detection of the resulting labelled material bound to the support will indicate the presence of the target nucleotide sequence in the sample.

Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

Various techniques can be employed for preparing a polynucleotide primer or other polynucleotide. They can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The polynucleotide primer can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as those employed in commercial kits for preparation of RNA (e.g. from Promega) and by the use of M13 for single stranded DNA as described by J. Messing (1983) *Methods Enzymol*, 101, 20–78.

Other methods of oligonucleotide synthesis include phosphotriester and phosphodiester methods (Narang, et al. (1979) *Meth. Enzymol* 68: 90) and synthesis on a support (Beaucage, et al. (1981) *Tetrahedron Letters* 22: 1859–1862) as well as phosphoramidate technique, Caruthers, M. H., et. al., "Methods in Enzymology," Vol. 54, pp. 287–314 (1988), and others described in "Synthesis and Applications of DNA and RNA," S. A. Narang, editor, Academic Press, New York, 1987, and the references contained therein.

In some instances, the 3'-end of a polynucleotide will be modified to prevent reaction with template dependent DNA polymerase or to append a binding sequence. The 3'-end can, for example, be modified by ligation of a dideoxynucleotide or a ribonucleotide followed by oxidation of the ribose with periodate followed by reductive amination of the resulting dialdehyde with borohydride and a bulky amine such as aminodextran.

The polynucleotide primer or other polynucleotides can be prepared by standard automated techniques.

As a matter of convenience, the reagents employed in the present invention can be provided in a kit in packaged combination with predetermined amounts of reagents for use in the present method. In assaying for a polynucleotide analyte in a sample, a kit useful in the present method can comprise, in packaged combination with other reagents, reagents for forming a target nucleotide sequence from a polynucleotide analyte, a polynucleotide having a sequence hybridizable with a sequence of the target nucleotide sequence, a ligase, and a polynucleotide primer, the latter two of which can be labeled or one of which can be bound to a support or can be provided with groups to render the sequence labeled or bound to a support. For use in a method of producing multiple copies, the kit will contain a polynucleotide primer. Either of the kits above can further include in the packaged combination nucleoside triphosphates such as deoxynucleoside triphosphates, e.g., deoxyadenosine triphosphate (dATP), deoxyguanosine triphosphate (dGTP), deoxycytidine triphosphate (dCTP) and deoxythymidine triphosphate (dTTP). The kit can further include a polynucleotide polymerase and members of a signal producing system and also various buffered media, some of which may contain one or more of the above reagents.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life will permit.

EXAMPLES

The invention is demonstrated further by the following illustrative examples.

| Definitions | |
|---|---|
| BAP | bacterial alkaline phosphatase |
| N.E.B. | New England Biolabs |
| AMP + PP | adenosine-5'-monophosphate and pyrophosphate |
| ATP | adenine triphosphate |
| ON | oligonucleotide |
| rev | reverse |
| BRL | Bethesda Research Laboratories |
| dpm | disintegrations per minute |
| pcp | 5'-, 3'-cytidine bisphosphate |
| C | cytosine |
| G | guanine |
| A | adenine |

EXAMPLE 1

MATERIALS AND METHODS

Enzymes and Chemicals

The restriction enzyme *Hind* III and BAP were purchased from Bethesda Research Laboratories (BRL). T4 polynucleotide kinase was purchased from Stratagene, and T4 DNA ligase was purchased in a highly concentrated form, 2000 u/µL, and at 400 u/µL from New England Biolabs (Catalog No. 202C, Lots 34, 39, 42, 43 and 202, Lot 32). 1 unit (defined by N.E.B.) is equal to 0.015 ATP-PP exchange unit (Weiss et al (1968) Supra. All enzymes were used under the conditions specified by the manufacturer, unless otherwise stated. Cyanoethyl phosphoramidites for DNA synthesis were obtained from Cruachem, Inc., and [$\gamma^{32}$P]ATP used in 5'-end-labeling of oligonucleotides was purchased from New England Nuclear (DuPont).

Chemical Synthesis of Oligonucleotides

Oligonucleotides were synthesized on a BioSearch 8650 DNA synthesizer through standard phosphoramidite methodology (Atkinson, et al (1984). In Gait, J. J. (ed.) Oligonucleotide Synthesis: A Practical Approach. IRL Press, Oxford England; and gel purified by electrophoresis on preparative polyacrylamide gels. The DNA was excised, elutied overnight in 0.1 M $NH_4CO_3$ at 37° C., and concentrated and de-salted using Sep-Pak $C_{12}$ cartridges (Waters Associates). Sequences are shown in Table II.

| OLIGONUCLEOTIDE | SEQUENCE |
|---|---|
| ON1 | 3'- GTTAATGTGTTCGAATTATGTAAGGAACGTACGGACGTCCAGCTGAGATC -5' |

| OLIGONUCLEOTIDE | SEQUENCE |
|---|---|
| ON2 | 3'- GTTAATGTGTTCGAATTATGTAAGGAACGTACGGACGTCCAGCTG -5' |
| ON3 | 3'- GTTAATGTGTTCGAATTATGTAAGGAACGTACGGACGTCC -5' |
| ON4 | 3'- GTTAATGTGTTCGAATTATGTAAGGAACGTACGGA -5' |
| ON5 | 3'- GTAATGTGTTCGAATTATGTAAGGAACGT -5' |
| ON6 | 5'- CAATTACACAAGCTTAATACATTCC -3' |
| ON1rev | 3'- CTAGAGTCGACCTGCAGGCATGCAAGAATGTATTAAGCTTGTGTAATTG -5' |
| ON6rev | 3'- CAATTACACAAGCTTAATACATTCC -5' |

Synthetic oligonucleotide sequences used in the ligation reactions ON1 through ON5, and ON6rev are donor molecules supplying the 5'phosphoryl end group. ON6 and ON1rev are acceptor molecules contributing the 3'-hydroxyl end group when base paired to any one of the donors. Underlined bases indicate region involved in base pairing with ON6 or ON6rev. The program OLIGO, which analyzes DNA/RNA sequences, was purchased from National Biosciences, Hamel, Minn.

Preparation of $5'-^{32}P$-labeled oligomers

Oligonucleotide sequences (ON1 through ON5, ON6rev) were 5'-end-labeled as described by Ausubel et a (1987). Current Protocols in Molecular Biology, Greene Publishing Associates, John Wiley and Sons, Inc., New York, Vol. 1, 3, 10.3. Reactions were typically carried out in 10–30 μL volumes in the presence of $[\gamma-^{32}P]ATP$ at 6000 Ci/mmole and 10 to 20 units of T4 polynucleotide kinase. Labeled oligonucleotides were separated from the unincorporated radioactive nucleotide on Nensorb-20 cartridges (DuPont). Overall efficiencies ranged from 60 to 85 percent, determined by excising bands from a polyacrylamide gel and counting in a liquid scintillation counter.

Ligation Reaction

To assay for ligase activity, a $5'-^{32}P$ donor sequence (ON1-ON5, ON6rev) was incubated with the acceptor sequence (ON6 or ON1rev) in 5 mM dithiothreitol, 1 mM ATP, ligase buffer (66 mM Tris-Cl, pH 7.5, 66 mM $MgCl_2$, and varying amounts of T4 DNA ligase in volumes of 20 or 40 μL. To anneal, the reactants were heated to 65° C. for 5 minutes in the ligation mix and allowed to cool to room temperature (24° C., 15–30 minutes) prior to the addition of ligase. Reactions were incubated with T4 DNA ligase at room temperature for at least 2 hours.

Polyacrylamide Gel Electrophoresis (PAGE)

Typically, 8–15% (w/v) gels were prepared from a 40% (w/v) solution of acrylamide (38%) and bis-acrylamide (2%; Amresco), 8 M urea (BRL), and IX TBE (89 mM Tris-borate, 89 mM boric acid, 2 mM EDTA). Reaction aliquots were heat denatured at 90° C. for 3 minutes in the presence of a formamide loading buffer (80% formamide, 0.1% xylene cyanol, 0.1% bromophenol blue, 50 mM Tris-borate, 1 mM EDTA), chilled on ice, and electrophoresed under conditions described by Maniatis et al. (1982) Molecular Cloning: A Laboratory Manual, Cold Spring Harbor University Press, Cold Spring Harbor, p. 185. The MSp I digest of pBR322 (New England Biolabs) was end-labeled with $^{32}P$ and used as a molecular weight standard. Product formation was visualized by autoradiography following exposure to Kodak X-OMAT TM AR diagnostic film.

Quantitation of Product Formation

Following autoradiography, appropriate radioactive bands were excised from the gel and placed into vials containing approximately 10 mLs of Ready Safe TM liquid scintillation fluid (Beckman). Samples were counted on a Beckman LS 2800 Liquid Scintillation instrument. Ligation yields were calculated by summing the $^{32}P$ dpm in both precursor and product bands and expressing the dpm in the product band as a percentage of the total. Ligation efficiencies were not calculated in every case, due to a contaminating phosphatase activity present in various lots of the concentrated ligase.

RESULTS

Ligation of a Synthetic, Partially Double-Stranded Substrate

The synthetic DNA construct depicted in FIG. 15 was originally designed as a negative control for ligase experiments ongoing in our lab. Preliminary results suggested that T4 DNA ligase was able to covalently link the two strands without the benefit of base-pairing to align the termini. To study this activity further, 1 picomole of $5'-^{32}P$-labeled ON1 annealed to 1.5 picomoles of ON6 was incubated with varying amounts of T4 DNA ligase and the results analyzed by polyacrylamide gel electrophoresis. Autoradiography showed the conversion of ON1 (50 mer) into a product 75 bases in length. The appearance of the product band seemed to correlate directly with the disappearance of the substrate in the presence of highly concentrated enzyme (FIG. 1A). Very little product was formed when the enzyme concentration was decreased 10-fold (FIG. 1B). No mobility shift was observed when either ON6 or the ligase (highest concentration) was omitted (FIG. 1C, 1D). FIG. 1 is an autoradiogram of a 15% denaturing polyacrylamide gel showing the conversion of ON1 (radiolabeled 50 mer) to a 75-base product in the presence of ON6 (25 met) and T4 DNA ligase. Product formation after 2, 4, and 20 hours of incubation with (A) 4000 units and (B) 400 units of T4 DNA ligase at room temperature. Faint product bands are visible on original autoradiogram at each timepoint in B. No detectable ligation occurs in the absence of ON6 (C) or enzyme (D). This is a 2.5 hr exposure at −70° C. with intensifying screens.

Yields increased approximately two-fold when the 5'-phosphoryl end-group was recessed. ON1 and ON6 were synthesized in the reverse orientation (ON1rev and ON6rev) to create a substrate (when annealed) with an extended 3'-hydroxyl group and a recessed 5'-phosphoryl group. In a volume of 20 μL, 2 picomoles of $^{32}P$-labeled ON6rev annealed to 3 picomoles of ON1rev were incubated with 2000 units of T4 DNA ligase for 2 hours at room temperature. Results are shown in FIG. 2 using the original construct under identical conditions as a control. FIG. 2 is an autoradiogram comparing product yields when the position of the 5'-phosphoryl end-group is either extended or recessed. Product yield is 24% when the original substrate, $^{32}P$-labeled ON1 and ON6, is used (A). Yields double when $^{32}P$-labeled ON6rev and ON1rev create a substrate in which the 5' end-group is recessed (B). Aliquots taken before adding ligase (−) and after a 2 hr incubation with 2000 units of T4 DNA ligase (+) were electrophoresed on a 15% denaturing polyacrylamide gel. Reactions were performed in parallel using identical buffers and enzyme concentrations.

Characterization of the Ligated Product

The standard assay for ligase activity measures the conversion of $^{32}$P-labeled 5'phosphomonoesters to diesters. In this form, the linkage is resistant to digestion with bacterial alkaline phosphatase. Although the products from our ligase reactions were phosphatase resistant, the assay does not differentiate between a stem-loop structure product and the possible circularization of the $^{32}$P-labeled oligonucleotide to its own 3'-end-group. Form ally, a circular 50 mer could electrophorese in the position of a linear 75 mer (see FIG. 16). A Hind III site incorporated into the base-paired region allowed us to predict the cleavage patte rn after enzymatic digestion:

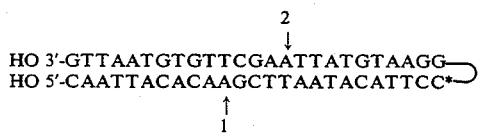

Complete digestion of the 75-base stem-loop (cuts at 1 and 2) would result in a radiolabeled fragment 51 bases in length. A limited digest, however, could release two additional fragments. A radiolabeled 65 mer would be expected if cleavage occurred at site 1 but not 2, whereas a 61-base fragment would be released if cleavage occurred at site 2 but not 1. A circularized product was not expected to be a substrate for the enzyme. As shown in FIG. 3, the mobilities of the major radiolabeled fragments released by digestion were as predicted for the stem-loop structure. The restriction pattern indicates that much of the product is completely digested, while a portion is partially cleaved at site 1, but not site 2. A minor amount of product is undigested. Overnight digestion drives most of the partially cleaved species into the lowest molecular weight band. FIG. 3 is a restriction digest of the ligated product with Hind III. Autoradiogram of 20% polyacrylamide gel shows the intact product in lane 1 and the products obtained after digestion with 10 units of Hind III for 1 hour at 37° C. in lane 2. From the mobilities of molecular weight markets, we estimate the restriction fragments to be 65 and 51 bases. A faint band corresponding to 61 bases is visible on the original autoradiogram. The gel was exposed to X-ray film overnight at −70° C. with intensifying screens. Prior to enzymatic digestion, the $^{32}$P-labeled 75 mer was eluted from a 15% polyacrylamide gel in 0.1 M ammonium bicarbonate (1 mL) overnight at room temperature. Following purification by Nensorb chromatography, the oligonucleotide was vacuum-dried in a Speed Vac Concentrator (Savant).

Effect of Single-Stranded DNA Length on Product Formation

Four oligonucleotides were synthesized (ON2 through ON5) to examine effects upon ligation yields due to the length of the unpaired 5'-end of the donor molecule. As shown above, each oligomer is 5, 10, 15, and 20 bases shorter than ON1 at the 5'-end. When substituted for ON1 in the ligase assay, the potential loops formed would be 20, 15, 10, and 5 bases in length, respectively. The four oligonucleotides were 5'-$^{32}$P end-labeled as described previously. In a volume of 20 μL, 2 picomoles of radiolabeled oligonucleotide annealed to 3 picomoles of ON6 were incubated with 2000 units of T4 DNA ligase. Aliquots taken before the addition of ligase and following a 2-hour incubation at room temperature were electrophoresed on a 15% (w/v) denaturing polyacrylamide gel. The results are shown in FIG. 4. FIG. 4. Autoradiogram (15% (w/v) gel) of ligation products using ON1 through ON5 as donor sequences. Odd numbered lanes (1, 3, 5, 7, and 9) represent each of the 5'$^{32}$P-labeled donors, ON5, ON4, ON3, ON2, and ON1, respectively. Fragment size (bases), as compared to molecular weight markets, is interpreted to be a) 30, b) 35, c) 40, d) 45, and e) 50. The even numbered lanes (2, 4, 6, 8, and 10) show product formation when these oligonucleotides are incubated with ON6 and T4 DNA ligase. Gel was exposed to X-ray film for 3.5 hr at −70° C. with intensifying screens. No detectable ligation occurred when ON5 was used in the assay (lane 2) despite the fact that the 5' base (T) could base-pair to the first unpaired A (same strand) to stabilize loop formation. This would properly align the termini to be joined creating a stable, but strained three-base loop. Approximately 7% of total $^{32}$P label was found in a product band (60 bases in length) when ON4 was the donor (lane 4). Forty-seven percent (47%) of the total $^{32}$P label was converted into product when ON3 was used (lane 6). ON2 is a poor donor for ligation with a 5% product yield (lane 8). In lanes 4 and 8, products formed (arrows) are shorter than expected (donor length plus 25 bases). This will be addressed in the Discussion. The control reaction, in which ON1 was ligated to ON6, displays the familiar shift in molecular weight from 50 to 75 bases. Efficiency of joining was calculated to be 27%.

DISCUSSION

The above results demonstrate the ability of ligase to effectively join short, synthetic DNAs without the benefit of complementarity to align the termini. The assay monitored the joining of a partially double-stranded substrate radiolabeled at the 5'-end. The resulting stem-loop product, now covalently attached, was analyzed by autoradiography following polyacrylamide gel electrophoresis under denaturing conditions. As shown in FIG. 1, higher enzyme concentrations and longer incubation times are required for efficient product formation. Because of the lack of complementarity, the interaction between the end-groups is weak, causing proper alignment to be a rare event. It is possible that in the presence of excess ligase, a stable complex is formed between enzyme and nucleic acid, whereby the adenyl-5'-phosphate intermediates accumulate. A similar explanation was proposed by Harvey and Wright (1972) Biochemistry, II: 2667–2671 to account for the joining of complementary oligonucleotides at temperatures above their T. The final ligation step is now dependent upon those events which bring the two end-groups into close proximity. When the substrate was altered such that the 5'-phosphate was recessed instead of extended, product formation doubled. Although adenylation of the extended 5'-phosphoryl end-group occurs, it has been concluded that the enzyme is better able to recognize and more readily adenylate the recessed end-group. This form of the substrate more closely resembles a strand in duplexed DNA. The ligation of this substrate is still incomplete, probably limited by the accessibility of the 3'=hydroxyl group.

Four additional oigonucleotides, shorter versions of ON1, were tested for their ability to act as donors in the ligase reaction when base paired to ON6. Some minimum length requirement associated with the observed ligation of the substrates was observed. Experimental results showed no evidence of product formation involving a five-base loop (ON5) and very little when the potential loop was 10 bases (ON4).

Products with 15- and 25-base loops were readily formed (ON3 and ON1), whereas the construct using ON2 (20-base loop) as the donor was a surprisingly poor substrate (see FIG. 4). The apparent preferential joining of ON1 and ON3 to ON6 is probably not explained solely on the basis of chain length. It is possible that base composition at the 5'-end of the donor is also a factor. Extensive studies reported by England and Uhlenbeck (1978) *ibid*, 17:2069-2076 involving oligoribonucleotides and T4 DNA ligase showed [5'$^{32}$P]pCp to be a more reactive donor. Both ON1 and ON3 terminate with a C at their 5'-ends, representing the reactions with the highest yields. This may also explain the shorter product bands observed in lanes 4 and 8 (indicated by arrows in FIG. 4). The 5'-ends of ON2 and ON4 are G and A, respectively. Thus, shorter oligonucleotides (a result of premature termination during synthesis) with a terminal C appear to be preferred donors, resulting in slightly shorter products when ligated to ON6.

Formation of the stem-loop product appears to proceed through an intramolecular joining event. A series of dilution experiments examined concentration effects upon product yields. Ligation efficiencies remained consistent as the substrate (ON1 and ON6) was diluted up to 100-fold. Reduced efficiency (less than 2-fold) was observed when a competing 50 mer, which does not hybridize to ON6 but could compete for ligation as a donor, was present during the ligation reactions at 100-fold molar excess. Titration of the enzyme in binding the excess 50 mer may account for the decrease in product formed. Finally, *Hind* III digestion of the gel purified 75-base product (ON1 and ON6) supports the conclusion that a covalent stem-loop product is being formed. These data strongly support product formation through a ligase-catayzed intramolecular reaction.

EXAMPLE 2

A 50 mer polydeoxynucleotide called oligomer 1 of sequence 5' dAA TTA CAC AAG CTT AAT ACA TTC CTT CGA GCT CGG TAG CCG GGG ATC CT 3' can be annealed to a 50 mer oligomer #2 of sequence 5' CTA GAG TCG ACC TGC AGG CAT GCA AGG AAT GTA TTA AGC TTG TGT AAT TG 3' using standard techniques. The resulting product will form 27 base pairs, with the remaining 23 bases of each oligomer component nonbase-paired. The 5'-hydroxyl of oligomer #2 is phosphorylated by polynucleotide kinase and Y-$^{32}$P ATP, and annealed to oligomer #1, the resulting molecule is a substrate for T4 DNA ligase in the presence of appropriate buffers and ATP. The yield of formation of the 100 mer is about 10% of the input oligomers using 2 pmoles annealed product, 30 Weiss units T4 DNA ligase in a standard DNA ligase buffer of 20 microliters total volume. A 100 base long "stem-loop" structure is formed.

A yield of ligation essentially 100% is achieved where the annealed substrate consists of a nonbase-paired 5' (phosphorylated) terminus on one oligomer and a base-paired 3' terminus on the other oligomer. A 25 mer oligodeoxynucleotide of sequence 5' CAA TTA CAC AAG CTT AAT ACA TTC C 3' and a 50 mer oligodeoxynucleotide of sequence 5' CTA GAG TCG ACC TGC AGG CAT GCA AGG AAT GTA TTA AGC TTG TGT AATTG 3' (oligomer 3 and 4, respectively) can be annealed to one another forming a 25-base pair region and a 5' 25 bases of oligomer 4 nonbase-paired. Oligomer 4 is 5' phosphorylated. T4 DNA ligase catalyzes from the annealed substrate the formation of a stem-loop structure by the covalent bond made between the 5' phosphate terminus of oligomer 4 and the 3' hydroxyl terminus of oligomer 3.

As a demonstration of the use of this technology, 100 femtomoles of the ligated oligomers 3 and 4 were temperature cycled in the presence of 120 picomoles oligomer 3, Taq DNA polymerase and excess dNTP's in a single primer amplification protocol.

100 femtomoles of the ligated oligomers 3 and 4, in the presence of 120 picomoles oligomer 3, 5 units Taq DNA polymerase, and 1 mM dNTPs were temperature cycled in a single promet amplification protocol. The 100 microliter reactions were cycled, 60 repetitions as follows: 94° C. - 30 seconds, 50° C. - 60 seconds, 72° C. - 30 seconds. Aliquots (10 microliters) were taken every 15 cycles.

Dot blot analysis of various timepoints of this reaction and controls demonstrated the amplification of a DNA species hybridizable to $^{32}$P labeled oligomer probe 5: 5' CTA GAG TCG ACC TGC AGG CAT 3'. Amplification after 60 cycles was approximately 1000-fold.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in molecular biology and related sciences are intended to be within the scope of the following claims.

What is claimed is:

1. A method of forming a single stranded polynucleotide having two segments that are non-contiguous and hybridizable with each other, said method comprising the steps of:
   (a) forming a partially single stranded duplex by hybridizing (1) a first polynucleotide sequence of about 30 to 5000 nucleotides in length and having one of a hydroxyl or phosphate group at its 3'-end with (2) a second polynucleotide sequence of at least 10 consecutive nucleotides in length that hybridizes with said first polynucleotide sequence and having the other of a hydroxyl or phosphate group at its 5'-end, wherein said partially single stranded duplex is comprised of a non-hybridized single stranded portion of at least one of said first and second polynucleotide sequences containing one of said ends and 10 to 25 nucleotides in length, and
   (b) ligating said ends within said duplex with an excess of T4 deoxyribonucleic acid ligase, thereby forming a single stranded polynucleotide having two segments that are non-contiguous and hybridizable with each other.

2. The method of claim 1 wherein said second polynucleotide sequence has a phosphate group at its 5'-end.

3. The method of claim 1 wherein said 5'-end of said second sequence is hybridized in said duplex.

4. The method of claim 3 wherein said 5'-end has a phosphate group.

5. The method of claim 1 wherein said partially single stranded duplex is comprised of a non-hybridized single stranded portion of each of said first and second polynucleotide sequences single stranded portion, each containing one of said ends and 5 to 25 nucleotides, wherein said 5'-end has a phosphate group.

6. A method of forming a single stranded polynucleotide having two segments that are non-contiguous and hybridizable with each other, said method comprising the steps of:
(a) combining (1) a first polynucleotide sequence having about 30 to 5000 nucleotides, (2) a second polynucleotide sequence having at least 10 consecutive nucleotides that can hybridize with said first polynucleotide sequence, and (3) a T4 deoxyribonucleic acid ligase wherein said ligase is present in a concentration in excess relative to the concentration of said first and second polynucleotide sequences;
(b) hybridizing said first and second polynucleotide sequences wherein one of the 3'-end of one of said sequences (sequence A) and the 5'-end of the other sequence (sequence B) is bound to the corresponding end of the hybridized first and second polynucleotide sequences by a single stranded sequence of 10 to 25 nucleotides in length; and
(c) forming a phosphodiester to and between the 5'-end of sequence B and the 3'-end of sequence A thereby forming a single stranded polynucleotide having two segments that are noncontiguous and hybridizable with each other.

7. The method of claim 6 wherein the 5'-end of sequence B has a phosphate group.

8. The method of claim 7 wherein the nucleotide at the 5'-end of sequence B is cytidine.

9. The method of claim 6 wherein the 3'-end of sequence A or the 5'-end of sequence B is part of said hybridized first and second polynucleotide sequences segment.

10. The method of claim 6 wherein said noncontiguous hybridizable segments contain from 10 to 100 nucleotides.

11. The method of claim 6 wherein said noncontiguous hybridized segments contain at least 10 nucleotides complementary to each other.

12. The method of claim 6 wherein said single stranded polynucleotide having two segments that are noncontiguous and hybridizable with each other is deoxyribonuceic acid (DNA).

13. The method of claim 6 wherein said ligase is present in a concentration of about 500 to 100 fold excess relative to the concentration of said first and second sequences.

14. A method for detecting the presence of a target polynucleotide sequence in a medium suspected of containing said target polynucleotide sequence, said method comprising the steps of:
(a) combining said medium with (1) a polynucleotide wherein said polynucleotide and said target polynucleotide sequence each have a segment of at least 10 nucleotides hybridizable with each other, the 5'-end of said polynucleotide or said target polynucleotide sequence having a phosphate group and (2) a T4 deoxyribonucleic acid ligase wherein said ligase is present in a concentration in excess relative to the concentrations of said polynucleotide and said target polynucleotide sequence,
(b) hybridizing said polynucleotide and said target polynucleotide sequence, if present, to form a partially single stranded duplex comprised of at least one non-hybridized single stranded portion 10 to 25 nucleotides in length at one end of one of said polynucleotide and said target polynucleotide sequence wherein a first terminal nucleotide of said non-hybridized single-stranded portion and a second terminal nucleotide of said other member of said duplex are ligated by said T4 deoxyribonucleic acid ligase, said second terminal nucleotide being proximal said first terminal nucleotide in said duplex,
(c) forming multiple copies of said target polynucleotide sequence ligated to said polynucleotide and detecting said copies, thereby detecting the presence of said target polynucleotide sequence.

15. The method of claim 14 wherein said multiple copies are formed by:
(a) hybridizing a single stranded polynucleotide primer at its 3'-end to a sequence within said segment of either said target polynucleotide sequence or said polynucleotide, both as part of said partially single stranded duplex comprised or said target polynucleotide sequence ligated to said polynucleotide,
(b) extending said polynucleotide primer in the presence of nucleoside triphosphates and a polynucleotide polymerase to provide a first extended polynucleotide primer,
(c) dissociating said first extended polynucleotide primer from said sequence within said hybridizable sequence,
(d) hybridizing said first extended polynucleotide primer with said polynucleotide primer,
(e) extending said polynucleotide primer along said first extended polynucleotide primer to provide a second extended polynucleotide primer,
(f) dissociating said second extended polynucleotide primer from said first extended polynucleotide primer, and
(g) repeating steps (d)–(f) above.

16. The method of claim 15 wherein said polynucleotide primer is 10 to 100 nucleotides in length.

17. The method of claim 14 wherein said target polynucleotide sequence is deoxyribonucleic acid (DNA).

18. The method of claim 14 wherein said first terminal nucleotide has a 5'-phosphate group and said second terminal nucleotide has a 3'-hydroxyl group.

19. The method of claim 14 wherein the 5'-end of said target polynucleotide sequence is separated from said hybridizable segment by 10 to 25 nucleotides.

20. The method of claim 18 wherein said first terminal nucleotide is cytidine (C).

21. The method of claim 14 wherein each of said segments has a sequence of from 10 to 100 nucleotides hybridizable with the other.

22. The method of claim 14 wherein each of said segments has at least a 10 nucleotide sequence complementary to the other.

23. The method of claim 14 wherein said polynucleotide is deoxyribonuceic acid (DNA).

24. The method of claim 14 wherein said ligase is present in a concentration of about 500 to 100 fold excess relative to the concentration of said polynucleotide and said target nucleotide sequences.

25. A method for detecting the presence of a polynucleotide analyte in a sample suspected of containing said polynucleotide analyte, said method comprising the steps of:
  (a) combining said sample with (1) a polynucleotide having at least a 10 nucleotide segment hybridizable with a segment of said polynucleotide analyte, and (2) a T4 deoxyribonucleic acid ligase in a concentration in excess relative to the concentrations of said polynucleotide and said polynucleotide analyte,
  (b) hybridizing said polynucleotide and said polynucleotide analyte, if present, to form a partially single-stranded duplex comprised of at least one nonhybridized single stranded portion 10 to 25 nucleotides in length at one end of said partially single stranded duplex wherein a first terminal nucleotide of said nonhybridized single-stranded portion and a second terminal nucleotide of the other member of said duplex are ligated by said T4 deoxyribonucleic acid ligase, said second terminal nucleotide being proximal said first terminal nucleotide in said duplex,
  (c) combining the sample suspected of containing said polynucleotide analyte ligated to said polynucleotide in said partially single-stranded duplex, nucleoside triphosphates and template-dependent polynucleotide polymerase and a polynucleotide primer at least the 3'-end of which hybridizes within said duplex with a sequence of either said polynucleotide analyte or of said polynucleotide,
  (d) forming an extended polynucleotide primer, and
  (e) examining said sample for the presence of extended polynucleotide primer thereby detecting the presence of said polynucleotide analyte.

26. The method of claim 25 wherein a portion of said polynucleotide primer is labeled with a first reporter group and a portion is labeled with a second reporter group.

27. The method of claim 25 wherein said polynucleotide analyte is deoxyribonucleic acid (DNA).

28. The method of claim 25 wherein said polynucleotide primer is 20 to 100 nucleotides in length.

29. The method of claim 25 wherein said template-dependent polynucleotide polymerass is a deoxyribonucleic acid (DNA) polymerase and said nucleotide triphosphates are deoxyadenosine triphosphate (ATP), deoxyguanosine triphosphate (dGTP), deoxycytidine triphosphate (dCTP), and deoxythymidine triphosphate (dTTP).

30. The method of claim 25 wherein said method is carried out at an excess concentration of said polynucleotide primer relative to the concentration of said polynucleotide.

31. The method of claim 25 wherein step (d) is repeated such that the number of molecules of said extended polynucleotide primer formed is increased by at least a factor of three.

32. The method of claim 25 wherein said polynucleotide is labeled with a reporter group.

33. The method of claim 32 wherein said reporter group is selected from the group consisting of, fluorescers, chemiluminescers, catalysts, co-enzymes, radioactive substances, amplifiable polynucleotide sequences, and small organic molecules.

34. The method of claim 25 wherein said polydeoxynucleotide primer is labeled with a ligand.

35. The method of claim 25 wherein said polynucleotide ligated to said polynucleotide analyte contains a sequence that when hybridized to its complementary sequence can be bound specifically by a receptor.

36. The method of claim 35 wherein said receptor is selected from the group consisting of repressors, activators, and restriction enzymes.

37. The method of claim 25 wherein said polynucleotide ligated to said polynucleotide analyte contains a sequence at its end that when hybridized to its complementary sequence, can be bound specifically by a receptor, and said extended polydeoxynucleotide primer is detected by binding said receptor to said extended polynucleotide primer.

38. The method of claim 25 wherein the 5'-end of said polynucleotide analyte is separated from said segment by 10 nucleotides.

39. The method of claim 25 wherein the nucleotide at the 5'-end of said polynucleotide analyte is cytidine (C).

40. The method of claim 25 wherein each of said segments has a sequence of from 10 to 100 nucleotides hybridizable with the other.

41. The method of claim 25 wherein said polynucleotide is deoxyribonuceic acid (DNA).

42. The method of claim 1 wherein said T4 deoxyribonucleic acid ligase is present in a concentration of about 200 to 100 fold excess relative to the concentration of said first and second polynucleotide sequences.

43. The method of claim 14 wherein said T4 deoxyribonucleic acid ligase is present in a concentration of about 200 to 100 fold excess relative to the concentration of said polynucleotide and said target polynucleotide sequence.

44. The method of claim 24 wherein said T4 deoxyribonucleic acid ligase is present in a concentration of about 200 to 100 fold excess relative to the concentration of said polynucleotide and said polynucleotide analyte.

45. The method of claim 25 wherein said T4 deoxyribonucleic acid ligase is present in a concentration of about 200 to 100 fold excess relative to the concentration of said polynucleotide and said polynucleotide analyte.

46. The method of claim 25 wherein said first terminal nucleotide has a 5'-phosphate group and said second terminal nucleotide has a 3'-hydroxyl group.

47. The method of claim 15 wherein said first terminal nucleotide has a 3'-hydroxyl group and said second terminal nucleotide has a 5'-phosphate group.

48. The method of claim 15 wherein said polynucleotide primer is said polynucleotide.

49. The method of claim 25 wherein said polynucleotide primer is said polynucleotide.

* * * * *